(12) United States Patent
Imamura et al.

(10) Patent No.: US 9,300,931 B2
(45) Date of Patent: Mar. 29, 2016

(54) IMAGE PICKUP SYSTEM

(71) Applicant: Panasonic Corporation, Osaka (JP)

(72) Inventors: Norihiro Imamura, Osaka (JP);
Michihiro Yamagata, Osaka (JP);
Tsuguhiro Korenaga, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 194 days.

(21) Appl. No.: 14/346,866

(22) PCT Filed: Jul. 24, 2013

(86) PCT No.: PCT/JP2013/004518
§ 371 (c)(1),
(2) Date: Mar. 24, 2014

(87) PCT Pub. No.: WO2014/017092
PCT Pub. Date: Jan. 30, 2014

(65) Prior Publication Data
US 2014/0300721 A1    Oct. 9, 2014

(30) Foreign Application Priority Data

Jul. 25, 2012 (JP) ................................. 2012-164857

(51) Int. Cl.
*H04N 9/47* (2006.01)
*H04N 5/765* (2006.01)
(Continued)

(52) U.S. Cl.
CPC ............... *H04N 9/643* (2013.01); *A61B 5/004* (2013.01); *A61B 5/0077* (2013.01); *A61B 5/0084* (2013.01); *A61B 5/444* (2013.01); *G06K 9/2018* (2013.01); *H04N 5/2256* (2013.01)

(58) Field of Classification Search
CPC ... H04N 5/2256; H04N 9/643; A61B 5/0077; A61B 5/004; A61B 5/444; A61B 5/0084; G06K 9/2018

USPC .................. 348/77, 61, 63, 64; 386/200, 201
See application file for complete search history.

(56) References Cited

U.S. PATENT DOCUMENTS

| | | | |
|---|---|---|---|
| 2007/0092160 A1 | 4/2007 | Fujii et al. |
| 2008/0194928 A1 | 8/2008 | Bandic et al. |

(Continued)

FOREIGN PATENT DOCUMENTS

| | | |
|---|---|---|
| CN | 101686819 A | 3/2010 |
| CN | 101977551 A | 2/2011 |

(Continued)

OTHER PUBLICATIONS

International Search Report for corresponding International Application No. PCT/JP2013/004518 mailed Aug. 20, 2013.
Chinese Search report for corresponding Chinese Application No. 201380003172.8 (with English Translation) dated Apr. 8, 2015.

*Primary Examiner* — Robert Chevalier
(74) *Attorney, Agent, or Firm* — Renner, Otto, Boisselle & Sklar, LLP

(57) ABSTRACT

An imaging system according to the present disclosure includes: a polarized light source which emits illuminating light including a component of light that oscillates parallel to a first polarization axis; an image capturing unit IP which is configured to get simultaneously first, second, third and fourth pieces of image information S101, S102, S104 including pieces of information about light beams that fall within first, second, third and fourth wavelength ranges, respectively, based on light beams that have returned at the same point in time from an object that is irradiated with the illuminating light, the light beam falling within the fourth wavelength range having been emitted from the polarized light source and reflected from the object, oscillating parallel to a second polarization axis that is different from the first polarization axis, and belonging to the same wavelength range as the component of the illuminating light.

18 Claims, 13 Drawing Sheets

(51) Int. Cl.
*H04N 9/64* (2006.01)
*A61B 5/00* (2006.01)
*G06K 9/20* (2006.01)
*H04N 5/225* (2006.01)

(56) References Cited

U.S. PATENT DOCUMENTS

2009/0278954 A1 11/2009 Kanamori et al.
2011/0013006 A1 1/2011 Uzenbajakava et al.
2012/0327423 A1* 12/2012 Hanebuchi ............. A61B 3/102
356/497

FOREIGN PATENT DOCUMENTS

| JP | 62076359 A | * | 4/1987 |
| JP | 2000-139846 A | | 5/2000 |
| JP | 2003-333608 A | | 11/2003 |
| JP | 2004-081735 A | | 3/2004 |
| JP | 2005-004468 A | | 1/2005 |
| JP | 2006-254331 A | | 9/2006 |
| JP | 2008-237243 A | | 10/2008 |
| JP | 2010-218258 A | | 9/2010 |

* cited by examiner

IMAGE PICKUP SYSTEM

TECHNICAL FIELD

The present application relates to an imaging system which shoots an organism such as a person's skin.

BACKGROUND ART

Imaging systems for observing an organism's skin have been developed. For example, Patent Document No. 1 discloses an imaging system which allows the user to observe spots on a person's skin using an UV light source including a polarization filter and an UV camera also including a polarization filter.

Such an imaging system includes a polarized light source which irradiates a biological tissue with light that oscillates in a predetermined polarization axis direction. The predetermined polarized light will be specular reflected light, of which the polarized light component is maintained, on the biological surface but will be scattered reflected light, of which the polarized light component has been disturbed, under the biological surface. That is why by arranging a polarization filter which transmits light that vibrates perpendicularly to the polarization axis of the polarized light source closer to an imaging device, an image representing the organism's subcutaneous tissue can be obtained.

Meanwhile, Patent Document No. 2 discloses an imaging system which generates a synthetic image to distinguish the skin state by shooting a UV ray irradiated image and a visible radiation irradiated image time-sequentially and then synthesizing those two images together.

CITATION LIST

Patent Literature

Patent Document No. 1: Japanese Laid-Open Patent Publication No. 2008-237243
Patent Document No. 2: Japanese Laid-Open Patent Publication No. 2004-81735

SUMMARY OF INVENTION

Technical Problem

The present inventors inspected those conventional skin-observing imaging systems rigorously to find that sometimes those systems were not suited to getting a movie, in particular. A non-limiting exemplary embodiment of the present application provides a skin-observing imaging system which can get a movie.

Solution to Problem

An imaging system according to an aspect of the present invention includes: a polarized light source which emits illuminating light including a component of light that oscillates parallel to a first polarization axis; an image capturing unit which is configured to get simultaneously first, second, third and fourth pieces of image information including pieces of information about light beams that fall within first, second, third and fourth wavelength ranges, respectively, based on light beams that have returned at the same point in time from an object that is irradiated with the illuminating light, the light beam falling within the fourth wavelength range having been emitted from the polarized light source and reflected from the object, oscillating parallel to a second polarization axis that is different from the first polarization axis, and belonging to the same wavelength range as the component of the illuminating light; a first arithmetic processing section which is configured to generate a first piece of color image information based on the first, second and third pieces of image information; and a second arithmetic processing section which is configured to generate a second piece of color image information by synthesizing each of the first, second and third pieces of image information with the fourth piece of image information.

Advantageous Effects of Invention

An aspect of the present invention provides an imaging system which allows the user to observe the skin of an organism, for example, in real time.

Figure 7:
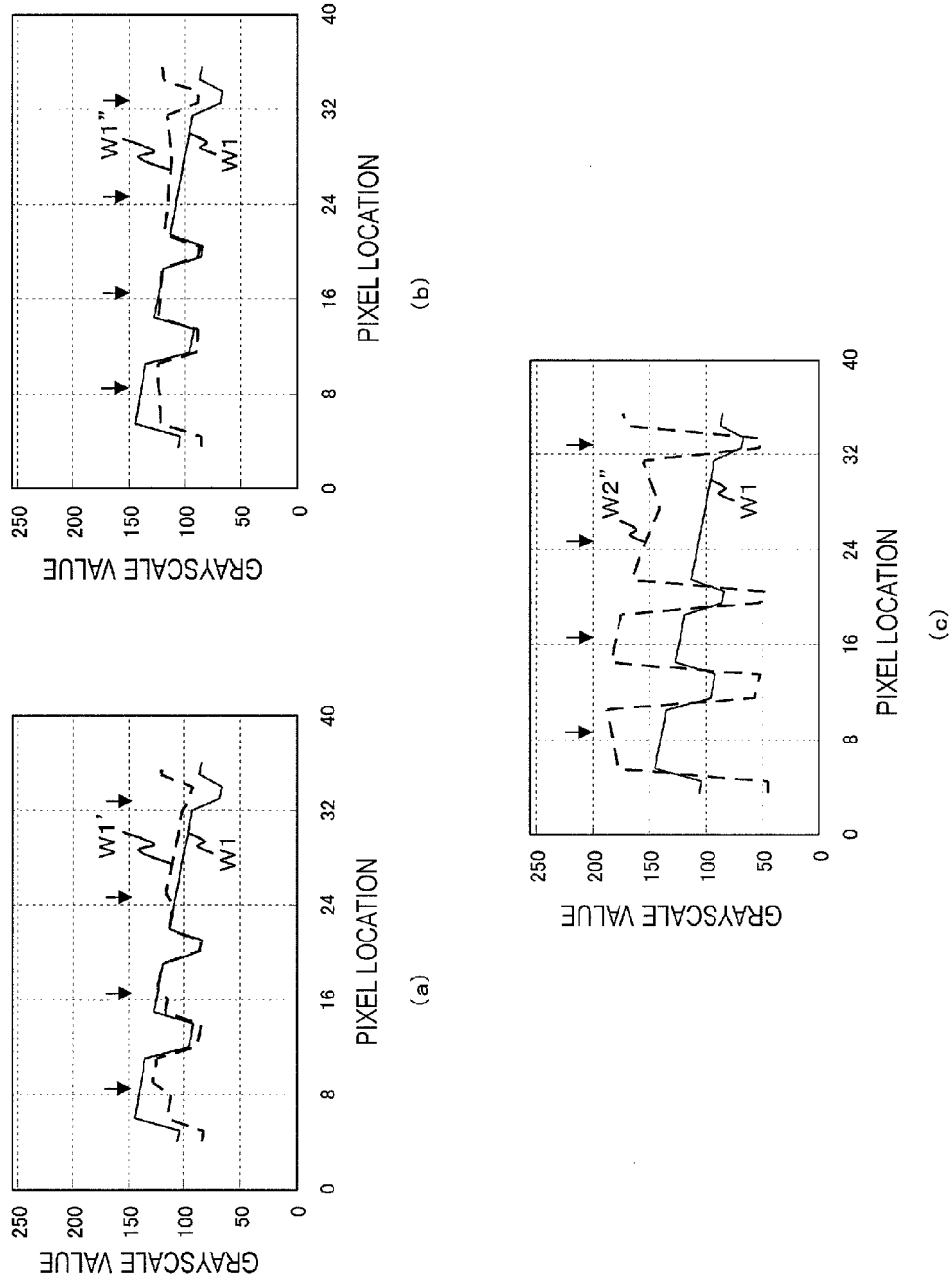

Portions (a) to (c) of FIG. 7 are graphs showing how to enhance the contrast according to the third embodiment.

Figure 8:
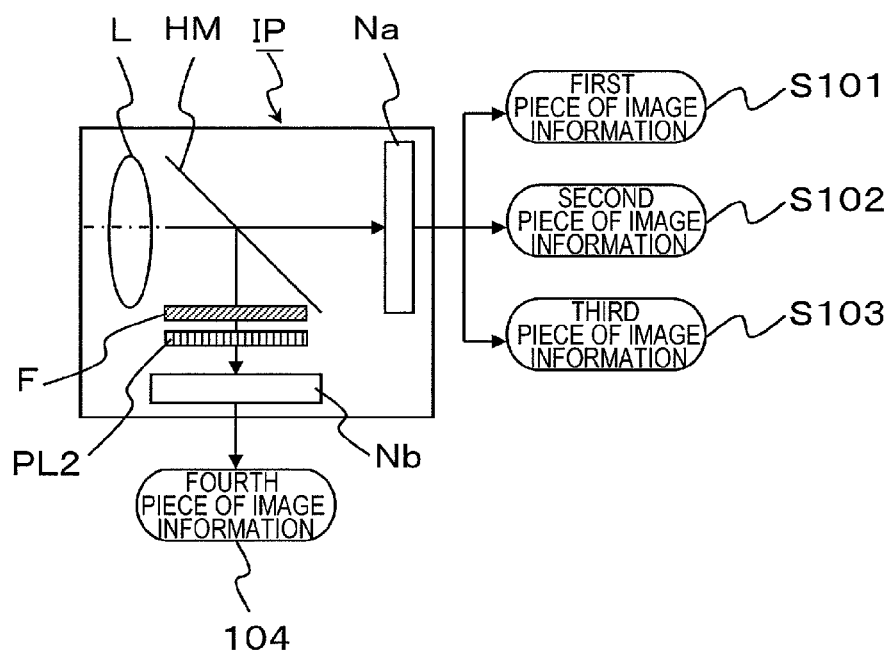

FIG. 8 is a schematic representation illustrating a configuration for an image capturing section for an imaging system according to a fourth embodiment.

Figure 9:
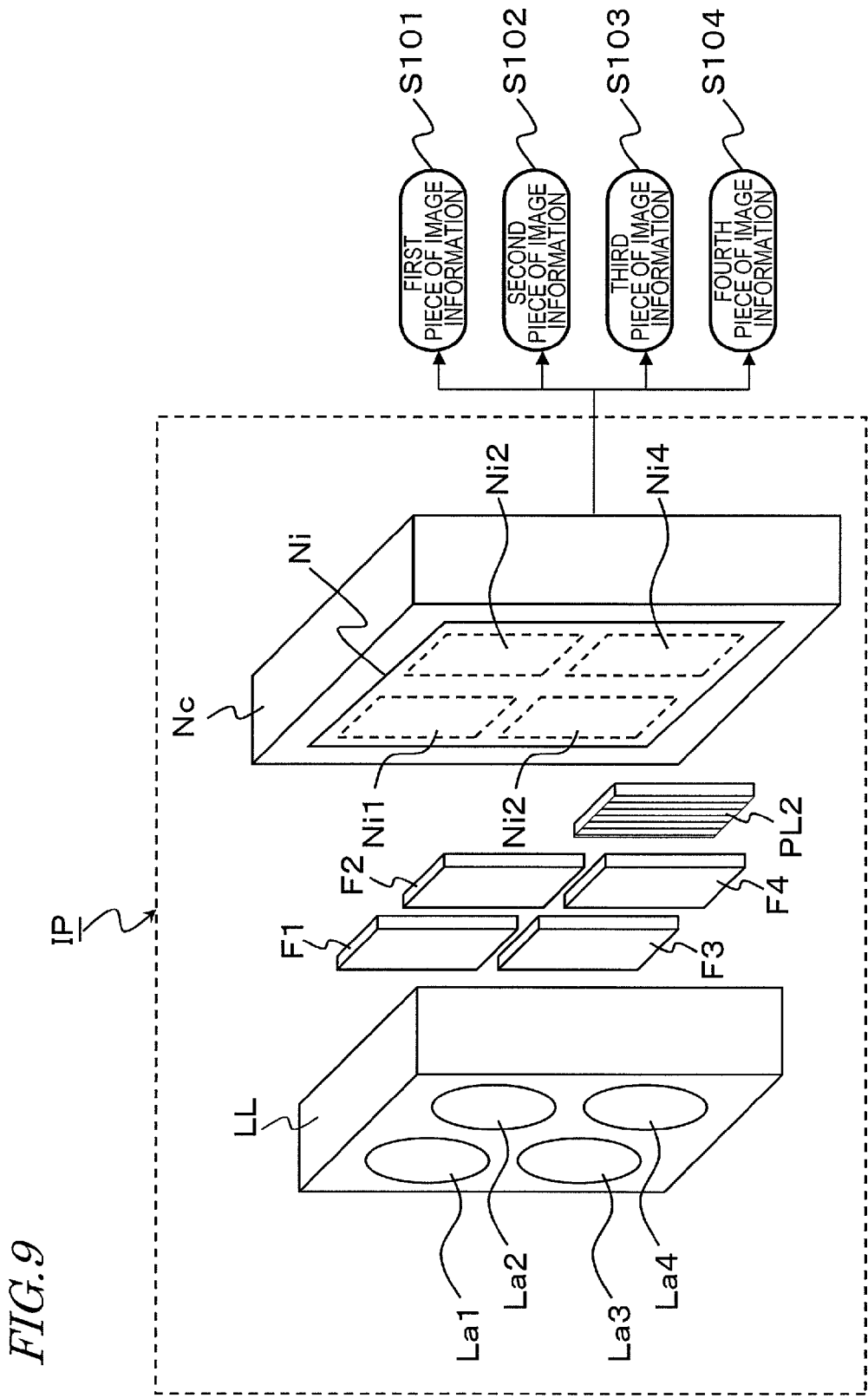

FIG. 9 is a schematic representation illustrating a configuration for an image capturing section for an imaging system according to a fifth embodiment.

Figure 10:
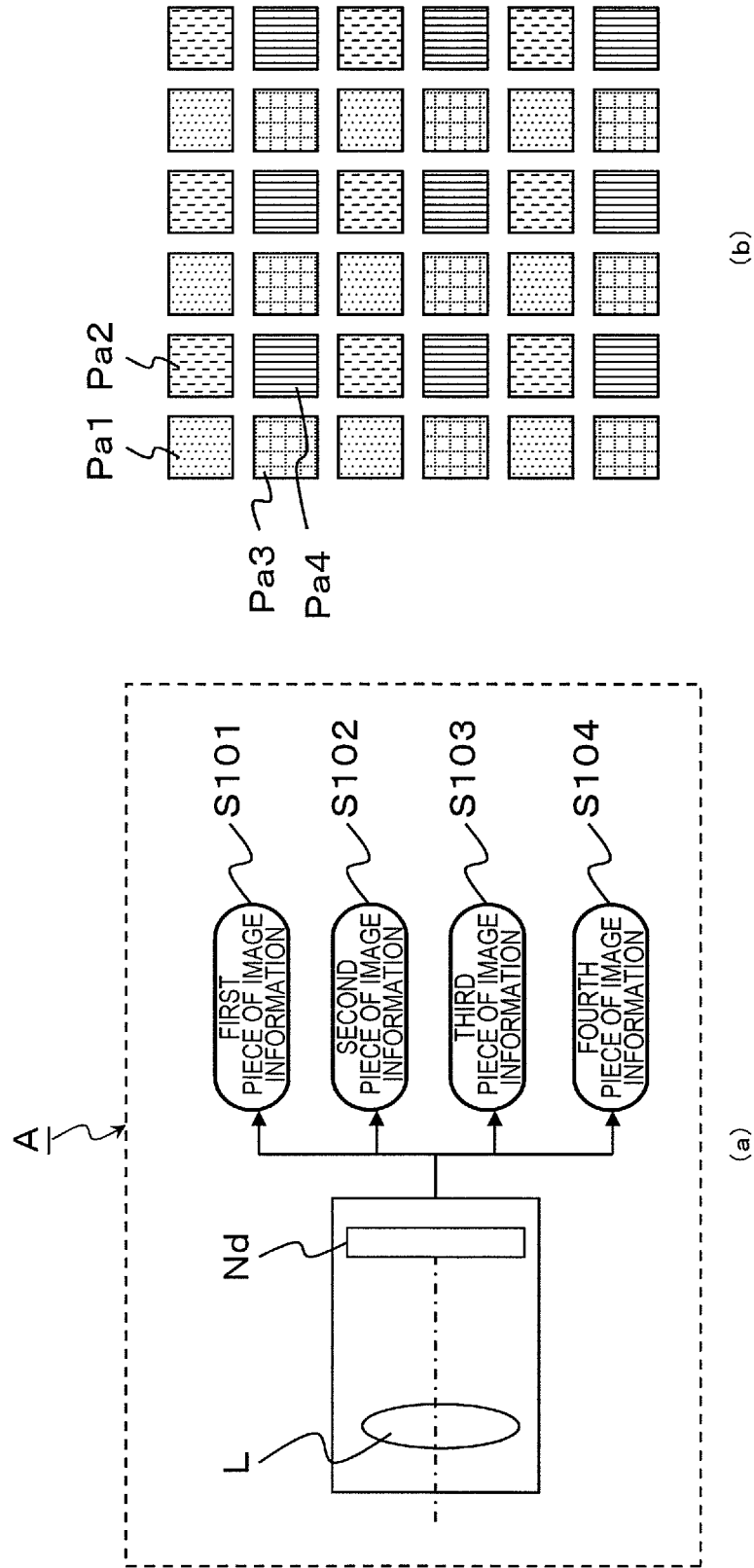

Portion (a) of FIG. 10 is a block diagram illustrating a configuration for an imaging device for an imaging system according to a sixth embodiment, and portion (b) illustrates an arrangement of pixels on an image sensor.

Figure 11:
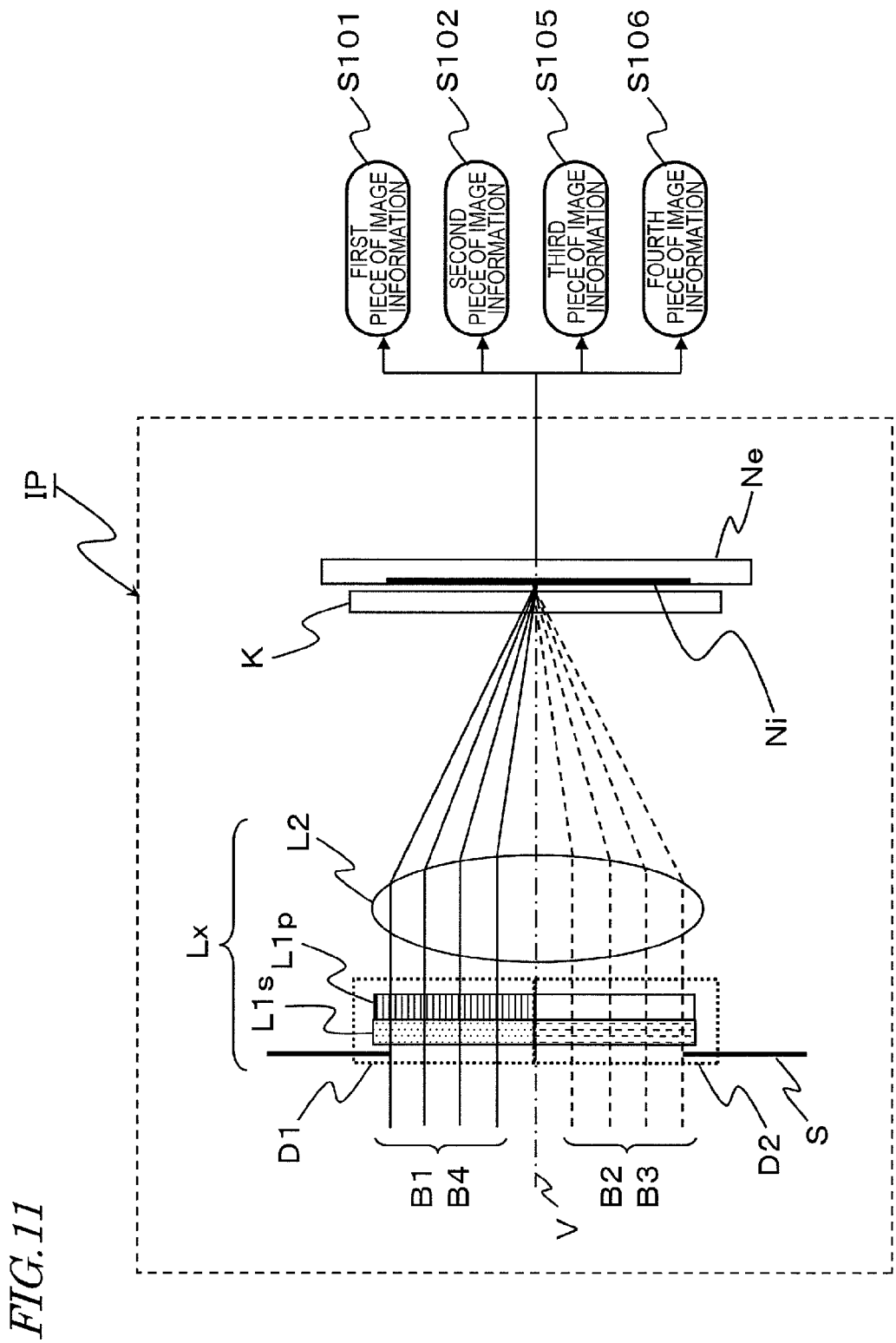

FIG. 11 is a schematic representation illustrating a configuration for an imaging device for an imaging system according to a seventh embodiment.

Figure 12:
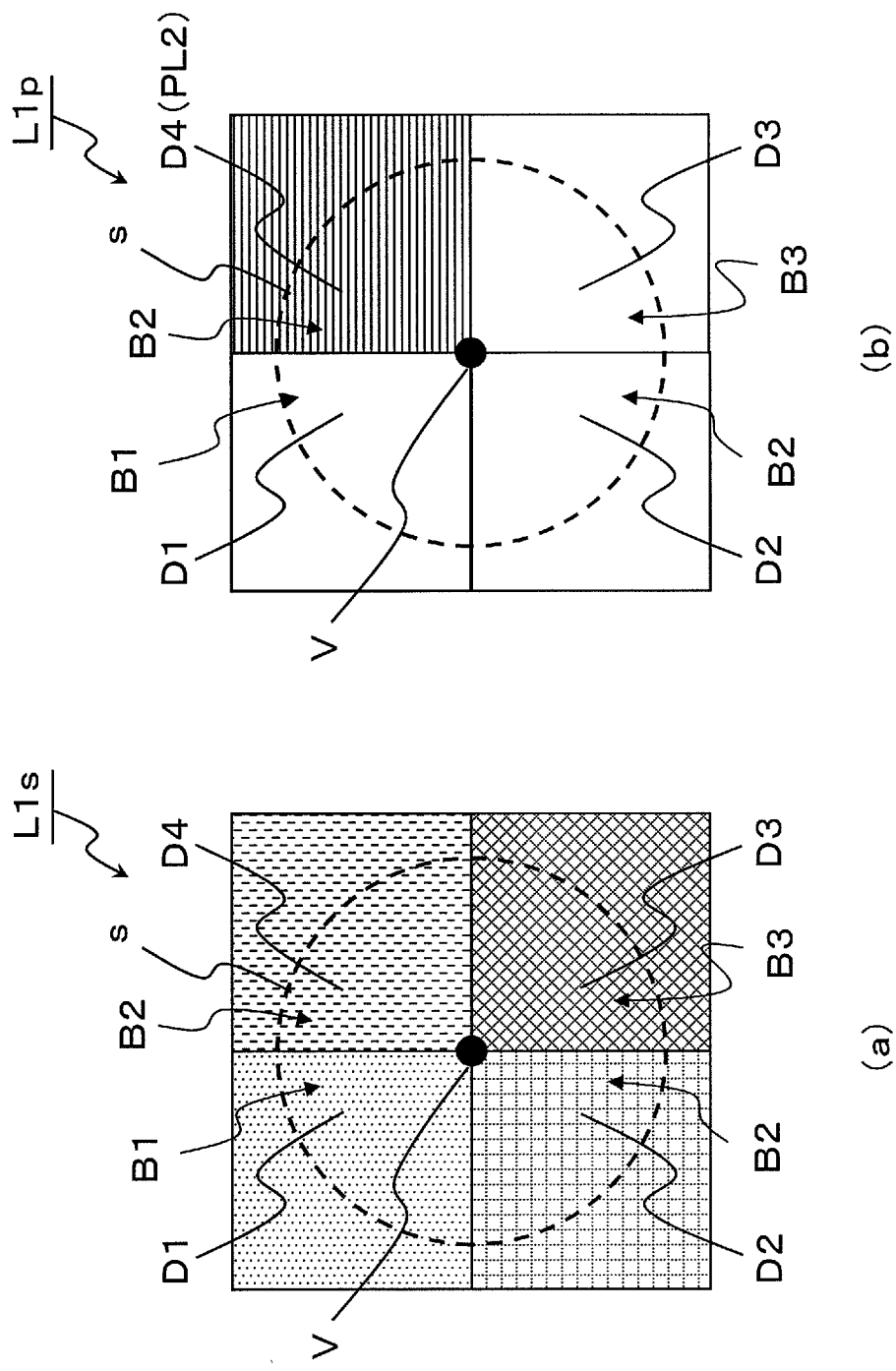

Portion (a) of FIG. 12 is a front view of the optical regions D1, D2, D3 and D4 of an optical element L1s according to the seventh embodiment as viewed from the object side, and portion (b) is a front view of the optical regions D1, D2, D3 and D4 of an optical element L1p as viewed from the object side.

Figure 13:
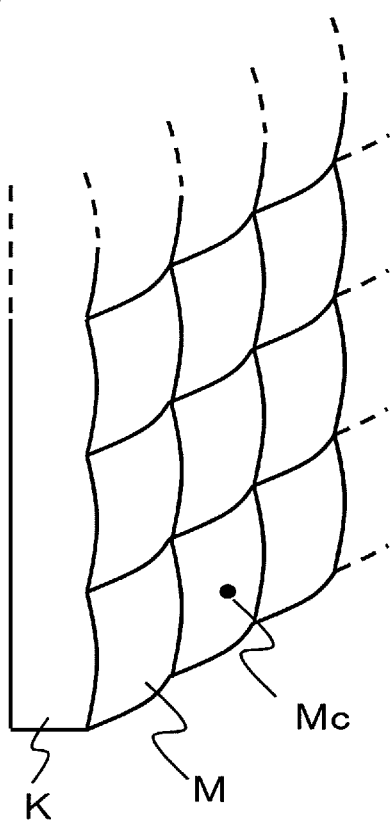

FIG. 13 is a perspective view illustrating an array of optical elements K according to the seventh embodiment.

Figure 14:
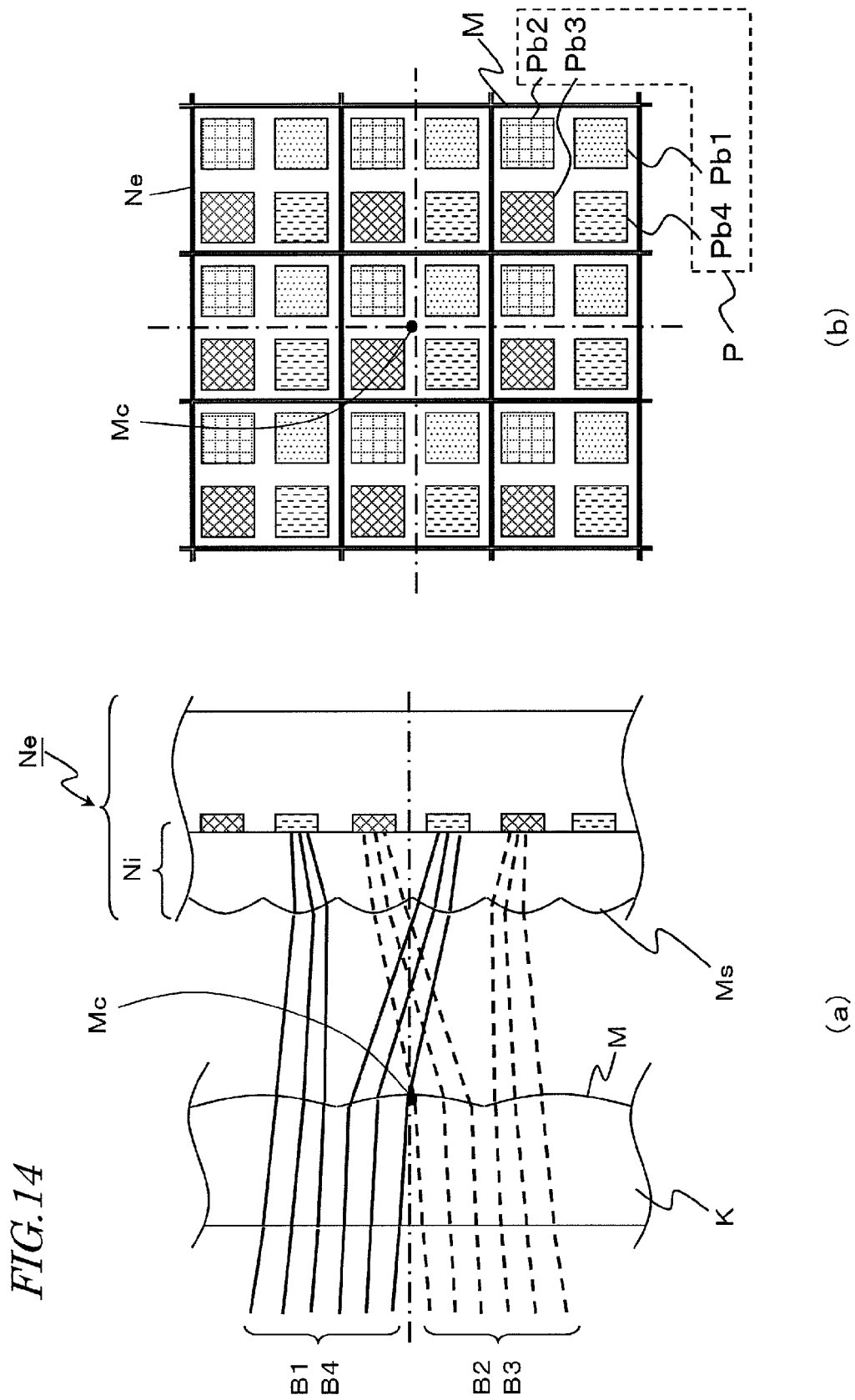

Portion (a) of FIG. 14 illustrates the array of optical elements K and the image sensor N according to the seventh embodiment on a larger scale, and portion (b) shows the relative position of the array of optical elements K with respect to pixels on the image sensor N.

Figure 15:
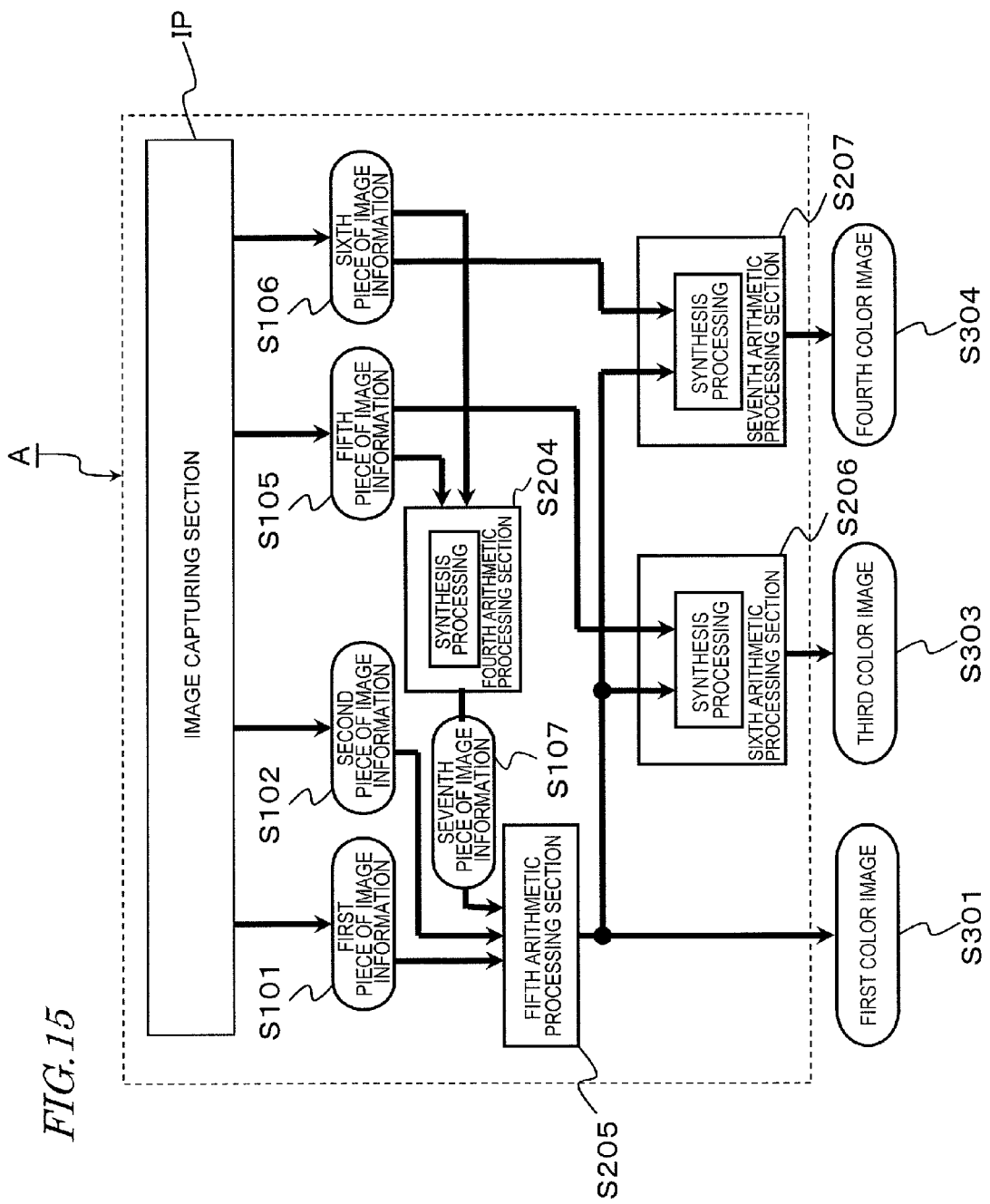

FIG. 15 is a block diagram illustrating an exemplary configuration for an imaging device for an imaging system according to an eighth embodiment.

Figure 16:
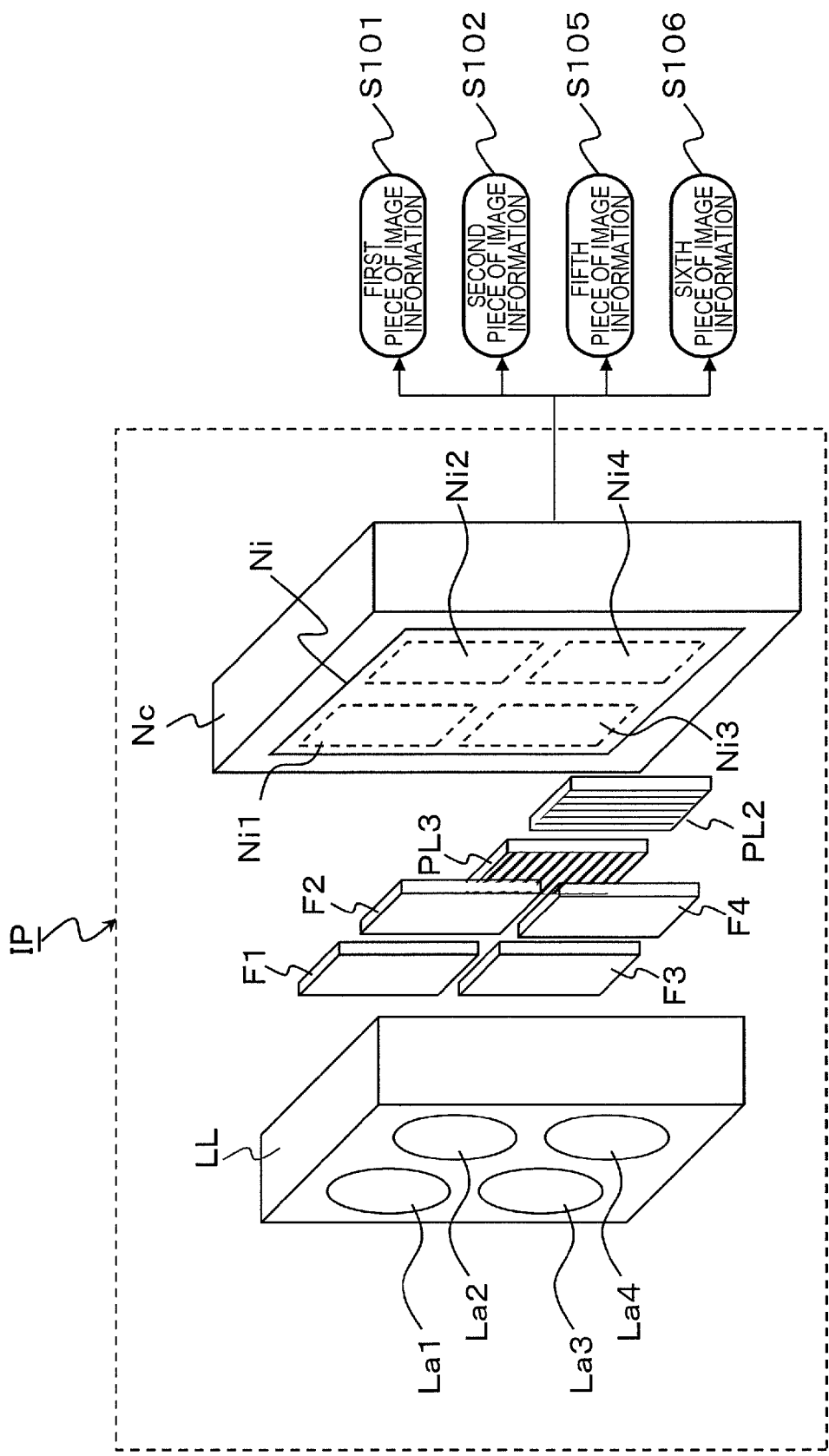

FIG. 16 is a schematic representation illustrating a configuration for an image capturing section for the imaging system according to the eighth embodiment.

DESCRIPTION OF EMBODIMENTS

The present inventors inspected those conventional imaging systems to find that they had their own problems. Specifically, according to Patent Document No. 1, polarization images falling within multiple wavelength ranges are gotten by a camera in which arranged are a plurality of polarized light sources falling within mutually different wavelength ranges and polarization filters which transmit light beams, of which the polarized light components are perpendicular to those of the polarized light sources. In this case, images falling within different wavelength ranges are gotten time-sequentially, and therefore, the imaging system of Patent Document No. 1 cannot be used effectively to capture a movie. In addition, since only ultraviolet illuminating light is used, those images cannot be compared to an image which has been gotten under visible radiation.

According to Patent Document No. 2, images under ultraviolet illuminating light and images under visible radiation are also gotten time-sequentially, and therefore, the system disclosed there cannot be used effectively to capture a movie, either. In addition, according to Patent Document No. 2, a synthetic image of the images under the ultraviolet illuminating light and the images under the visible radiation is generated based on a signal representing the difference between those images under the ultraviolet illuminating light and the images obtained by adjusting the tone of the images under the visible radiation into violet. That is why that synthetic image comes to have a different tone and a different grayscale than those of a normal color image. For that reason, to determine whether or not a spot detected is actually a spot of the skin, the synthetic image needs to be compared side by side to original images yet to be synthesized together. Consequently, if those images are presented side by side on a display, for example, each of those images comes to have just a small amount of information, which is a problem.

Thus, in order to overcome these problems with the prior art, the present inventors invented a novel imaging system to shoot the skin of an organism, for example. An imaging system according to an aspect of the present invention is as follows:

An imaging system according to an aspect of the present invention includes: a polarized light source which emits illuminating light including a component of light that oscillates parallel to a first polarization axis; an image capturing unit which is configured to get simultaneously first, second, third and fourth pieces of image information including pieces of information about light beams that fall within first, second, third and fourth wavelength ranges, respectively, based on light beams that have returned at the same point in time from an object that is irradiated with the illuminating light, the light beam falling within the fourth wavelength range having been emitted from the polarized light source and reflected from the object, oscillating parallel to a second polarization axis that is different from the first polarization axis, and belonging to the same wavelength range as the component of the illuminating light; a first arithmetic processing section which is configured to generate a first piece of color image information based on the first, second and third pieces of image information; and a second arithmetic processing section which is configured to generate a second piece of color image information by synthesizing each of the first, second and third pieces of image information with the fourth piece of image information.

The center wavelength of the fourth wavelength range may be shorter than the center wavelength of any of the first, second and third wavelength ranges.

The fourth wavelength range may be the same as the third wavelength range and the center wavelength of the third and fourth wavelength ranges may be shorter than the center wavelength of any of the first and second wavelength ranges.

Each of the first, second, third and fourth wavelength ranges may be a visible radiation wavelength range.

Each of the first, second, and third wavelength ranges may be a visible radiation wavelength range and the fourth wavelength range may be a near-ultraviolet wavelength range.

The imaging system may further include a third arithmetic processing section which is configured to perform the processing of enhancing the contrast of the fourth piece of image information before the second arithmetic processing section performs the synthesis processing.

Before enhancing the contrast, the third arithmetic processing section may calculate the average of grayscale values for each image block with a predetermined size with respect to the fourth piece of image information, and may adjust the gain of the grayscale value of each pixel in the image block based on the ratio of a predetermined normalized grayscale value to the average.

The synthesis processing may include multiplication processing.

The image capturing unit may include first and second image sensors, the first, second and third pieces of image information may be obtained by the first image sensor, and the fourth piece of image information may be obtained by the second image sensor.

The image capturing unit may further include an optical path splitting structure which splits a light beam that has come from the object into an optical path leading to the first image sensor and another optical path leading to the second image sensor.

The image capturing unit may include an image sensor, which may get the first, second, third and fourth pieces of image information.

The image capturing unit may further include: a lens array in which four lenses are arranged to form an array; and a spectral filter which transmits information about light beams falling within the first through fourth wavelength ranges and which is arranged so that those four light beams are associated one to one with respective optical paths of the four lenses, and the image sensor may have four image capturing areas which are associated one to one with the four lenses.

The image sensor may include: a plurality of photoelectric conversion sections which are arranged in a planar pattern; first to fourth spectral filters which are arranged on the plurality of photoelectric conversion sections to transmit the light beams falling within the first to fourth wavelength ranges, respectively; and a plurality of polarization filters which are arranged on a photoelectric conversion section where the fourth spectral filter is arranged and which have the second polarization axis.

The image capturing unit may include: a lens optical system; and an array of optical elements which is arranged between the lens optical system and the image sensor. The image sensor may include first, second, third and fourth sets of photoelectric conversion sections on which light that has passed through the lens optical system is incident. The lens optical system may have four optical regions which include first, second, third and fourth optical regions that transmit light beams falling within the first, second, third and fourth wavelength ranges, respectively. The fourth optical region transmits mostly a light beam oscillating parallel to the second polarization axis. The array of optical elements may make the light beams that have passed through the first, second, third and fourth optical regions incident onto the first, second, third and fourth sets of photoelectric conversion sections, respectively.

The imaging system may further include a display device which displays the image that has been gotten by the image capturing section.

The polarized light source may include a light source which emits light falling within the visible radiation wavelength range and a polarization filter which is arranged to transmit the light that has been emitted from the light source and which has a first polarization axis.

The polarized light source may include four light sources which emit light beams falling within the first, second, third and fourth wavelength ranges, respectively, and a polarization filter which has a first polarization axis. The polarization filter may be arranged so that only the light beam that has come from the light source that emits the light beam falling within the fourth wavelength range is transmitted through the polarization filter.

An imaging system according to another aspect of the present invention includes: a polarized light source which emits illuminating light including a component of light that oscillates parallel to a first polarization axis; an image capturing unit which is configured to get first, second, fifth and sixth pieces of image information including pieces of information about light beams that fall within first, second, third and third wavelength ranges, respectively, based on light beams that have returned at the same point in time from an object that is irradiated with the illuminating light, the light beam falling within the third wavelength range having been emitted from the polarized light source and reflected from the object, and oscillating parallel to either the first polarization axis or a second polarization axis that is different from the first polarization axis; a fourth arithmetic processing section which is configured to generate a seventh piece of image information, including a piece of information about the light beam falling within the third wavelength range, based on the fifth and sixth pieces of image information; a fifth arithmetic processing section which is configured to generate a first piece of color image information based on the first, second and seventh pieces of image information; a sixth arithmetic processing section which is configured to generate a third piece of color image information by synthesizing the first piece of color image information and the fifth piece of image information together; and a seventh arithmetic processing section which is configured to generate a fourth piece of color image information by synthesizing the first piece of color image information and the sixth piece of image information together.

Hereinafter, embodiments of an imaging device according to the present invention will be described with reference to the accompanying drawings.

Embodiment 1

Figure 1:
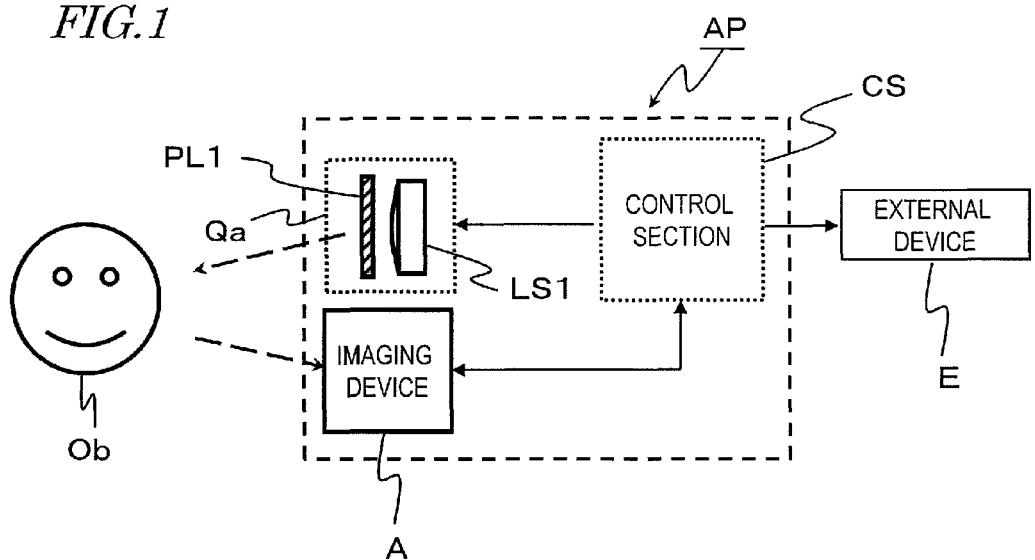
FIG. 1 is a schematic representation illustrating a configuration for an imaging system as a first embodiment of the present invention.

FIG. 1 is a schematic representation illustrating a configuration for an imaging system AP as a first embodiment. The imaging system AP shown in FIG. 1 includes an imaging device A, a polarized light source Qa, and a control section CS. In this embodiment, the polarized light source Qa includes a light source LS1 which emits visible radiation and a polarization filter PL1 which is arranged so as to transmit the light that has been emitted from the light source LS1. The polarization filter PL1 has a first polarization axis which is parallel to a first direction. The light emitted from the polarized light source Qa is polarized light falling within the visible radiation range and oscillating in the first direction. The polarized light source Qa includes light beams falling within first, second, third and fourth wavelength ranges, among which at least the light beam falling within the fourth wavelength range needs to be light oscillating in the first direction. That is to say, the illuminating light emitted from the polarized light source Qa has only to include a component falling within the fourth wavelength range and oscillating in only the first direction. And not all of the light emitted from the polarized light source Qa has to be polarized light but the light may include non-polarized light, too. For example, the first, second, third and fourth wavelength ranges may be the colors red, green, blue and violet wavelength ranges of 620-750 nm, 495-570 nm, 450-495 nm and 380-450 nm, respectively.

For example, if the light source LS1 emits white light, the white light includes light beams falling within the first, second, third and fourth wavelength ranges described above. In such a situation, the polarization filter PL1 may be arranged with respect to the light source LS1 so as to transmit the white light emitted, or the light source LS1 may include four independent light-emitting elements or light sources that emit light beams falling within the first, second, third and fourth wavelength ranges, respectively. In the latter case, the polarization filter PL1 needs to be provided for at least the light-emitting element or light source which emits the light beam falling within the fourth wavelength range.

The control section CS controls the imaging device A and the polarized light source Qa and also controls the input and output of data to/from an external device E. The external device E may be a storage device such as a memory which saves an image supplied from the imaging system AP, a display device which displays the image, a personal computer which processes the image, or a combination thereof. If a display device is added as the external device E, an image representing a person's skin, for example, can be observed in real time.

Figure 2:
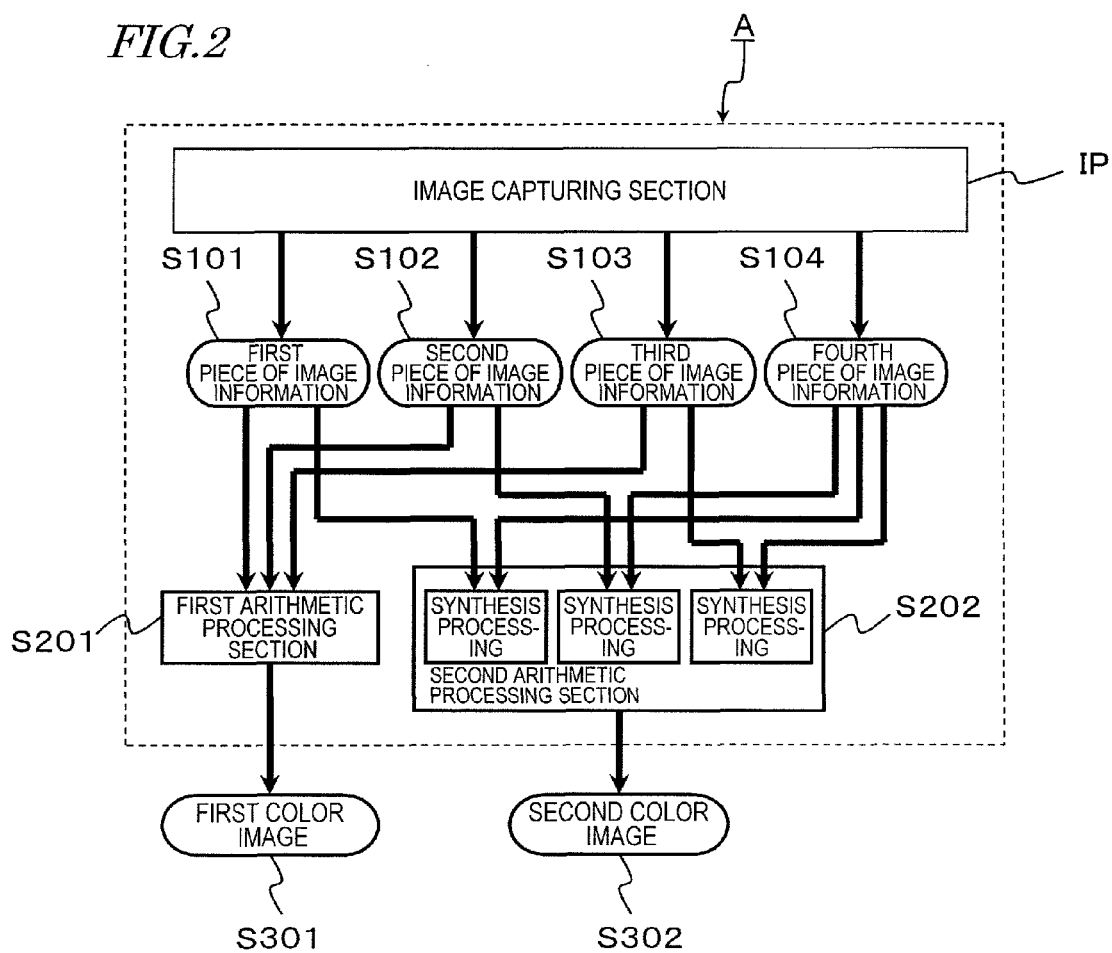
FIG. 2 is a block diagram illustrating an exemplary configuration for the imaging device in the imaging system of the first embodiment.

FIG. 2 is a block diagram illustrating an exemplary configuration for the imaging device A, which includes an image capturing unit IP and first and second arithmetic processing sections S201 and S202.

Figure 3:
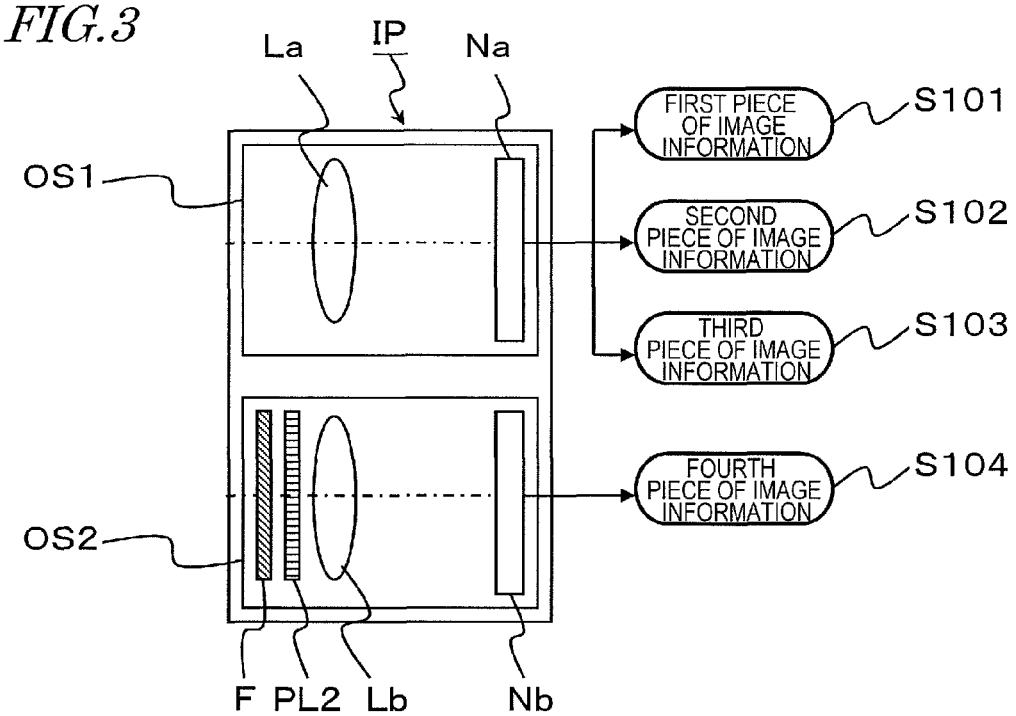
FIG. 3 is a schematic representation illustrating an exemplary configuration for the image capturing section of the imaging system of the first embodiment.

FIG. 3 is a schematic representation illustrating an exemplary configuration for the image capturing unit IP shown in FIG. 2. According to this embodiment, the image capturing unit IP includes first and second image capturing sections OS1 and OS2, and the object (not shown) is shot by the first and second image capturing sections OS1 and OS2.

The first image capturing section OS1 includes a first lens optical system La and a first image sensor Na. In this embodiment, the first image sensor Na is a color image sensor, and obtains first, second, and third pieces of image information S101, S102 and S103 including pieces of information about light beams falling within the first, second, and third wavelength ranges, respectively. As described above, the first, second, and third wavelength ranges are mostly comprised of the colors red, green and blue wavelength ranges, respectively. For example, just like an ordinary color image sensor, the first image sensor Na includes photoelectric conversion sections which are arranged two-dimensionally as pixels, and color filters which are respectively provided for three or four pixels (or photoelectric conversion sections) that together form a single picture element of a color image and which transmit light beams falling within the first, second, and third wavelength ranges, respectively.

The second image capturing section OS2 includes a band-pass filter F which transmits mostly a light beam falling within the fourth wavelength range, a second polarization filter PL2 which has a second polarization axis that is parallel to a second direction and which transmits mostly a light beam that oscillates in the second direction, a second lens optical system Lb, and a second image sensor Nb. The second polarization axis intersects at right angles with the first polarization axis of the first polarization filter provided for the polarized light source Qa shown in FIG. 2. The second image sensor Nb may be a monochrome image sensor, for example, has a piece of information about the light beam falling within the fourth wavelength range, and obtains image information S104 including a piece of information about the light beam oscillating in the second polarization axis direction. Also, as described above, the fourth wavelength range is a wavelength range including mainly the color violet wavelength range that falls within the visible radiation wavelength range. That is to say, the center wavelength of the fourth wavelength range is shorter than that of any of the first, second, and third wavelength ranges.

In this case, each of these lens optical systems La and Lb may consist of either a single lens or multiple lenses as well. In the example illustrated in FIG. 2, the lens optical systems La and Lb are each comprised of a single lens.

Next, it will be described how this imaging system AP works and in what procedure the imaging system AP shoots the skin of an organism, for example. First of all, the light emitted from the polarized light source Qa shown in FIG. 1 reaches the object Ob. The polarization filter PL1 of the polarized light source Qa transmits most of a light beam that oscillates parallel to the first polarization axis and absorbs most of a light beam that oscillates perpendicularly to the second polarization axis. That is why the object Ob is irradiated with only a light beam that oscillates parallel to the first polarization axis.

The object Ob may be a person's face skin, for example. In the following description of this embodiment, the object Ob is supposed to be a person's skin face. Some components of the light that has reached the face skin (as an exemplary object Ob) are reflected, but other components of the light are absorbed. And the imaging device A gets an image of the object Ob based on those reflected components. The light reflected from the face skin include components which are reflected from the surface of the face skin and components which have entered the inside of the face skin, have been internally scattered a number of times, and then are reflected from different points from the point of incidence. In this description, the "inside of the face skin" refers herein to his or her cuticle region. Where a spot is observed in the cuticle region, melanin has been produced. The light that has entered the cuticle, particularly a light beam falling within the color blue to near-violet (UVA, UVB) wavelength range, is attenuated by the melanin.

The light reflected from the surface of the face skin further includes specular-reflected components and diffuse-reflected components. Those components that are specular-reflected from the surface of the face skin maintain their polarization state. On the other hand, those components that are diffuse-reflected from the surface of the face skin and those components that have entered the inside of the face skin and that are reflected elsewhere have no-polarization state with disturbed polarization states, i.e., become non-polarized light.

That is why each of the first, second, and third pieces of image information S101, S102 and S103 which include pieces of information about the light beams falling within the first, second, and third wavelength ranges and which have been obtained by the first image capturing section OS1 includes the components of the light that has been specular-reflected from the face skin, the components of the light that has been diffuse-reflected from the surface of the face skin, and the components of the light that has entered the inside of the face skin and are reflected elsewhere, because an image of the object Ob is going to be captured with light that oscillates in every direction. The color image to be generated based on these pieces of image information is the same as an image which has been captured with an ordinary color camera. That is why a color image to be generated based on the piece of image information that has been obtained by the first image capturing section OS1 includes the components that have been specular-reflected from the face skin (i.e., components representing unwanted shine of the face skin), and therefore, it is difficult to sense a decrease in luminance due to the presence of a spot.

On the other hand, as for the fourth piece of image information obtained by getting the object Ob shot by the second image capturing section OS2, most of those components that have been specular-reflected from the face skin (i.e., components representing unwanted shine of the face skin) have been cut by the second polarization filter PL2 and the information includes information about the light beam falling within the fourth wavelength range that is the color violet wavelength range. That is why on an image generated based on the fourth piece of image information, a spot on the face skin which is rather hard to sense with the naked eye can be sensed easily.

As can be seen from the foregoing description, this image capturing unit IP is configured to obtain simultaneously first, second, and third pieces of image information S101, S102 and S103 including pieces of information about light beams falling within the first, second, and third wavelength ranges, respectively, and a fourth piece of image information S104 which allows the viewer to sense the state of a spot on the face skin easily, in order to generate an ordinary color image. In this description, "simultaneously" means that those first, second, third and fourth pieces of image information S101, S102, S103 and S104 are obtained based on the light beams that have been emitted at the same point in time from the polarized light source Qa and then reflected from the object. However, these pieces of image information do not have to be generated completely simultaneously but may also be generated with a certain time lag as long as a movie can be generated with no problem.

Next, the image processing flow will be described. As shown in FIG. 2, the first arithmetic processing section S201 is configured to generate a first color image S301 based on the first, second and third pieces of image information S101, S102 and S103 including pieces of information about light beams falling within the first, second, and third wavelength ranges, respectively.

The second arithmetic processing section S202 is configured to generate a second piece of color image information by synthesizing each of the first, second and third pieces of image information S101, S102 and S103 with the piece of image information S104 including a piece of information about a light beam that oscillates in the second polarization axis direction and that falls within the fourth wavelength range.

To carry out the signal processing described above, the first and second arithmetic processing sections S201 and S202 of the imaging device A may be either implemented as dedicated integrated circuits or a combination of a microprocessor (MPU), a memory and a software program which is stored in the memory, for example, and which processes the signal in the signal processing procedure described above. Alternatively, those arithmetic processing sections may also be a combination of both of them. Also, in order to carry out the signal processing described above, the first and second image sensors Na and Nb may output the first, second, third and fourth pieces of image information S101, S102, S103 and S104 which are digital data that have been A/D converted. Alternatively, first through seventh arithmetic processing sections S201 to S207 may convert the first, second, third and fourth pieces of image information S101, S102, S103 and S104 which are analog data into digital data. The third through seventh arithmetic processing sections S203 through S207 of the embodiments to be described below may also have the same configuration.

Figure 4:
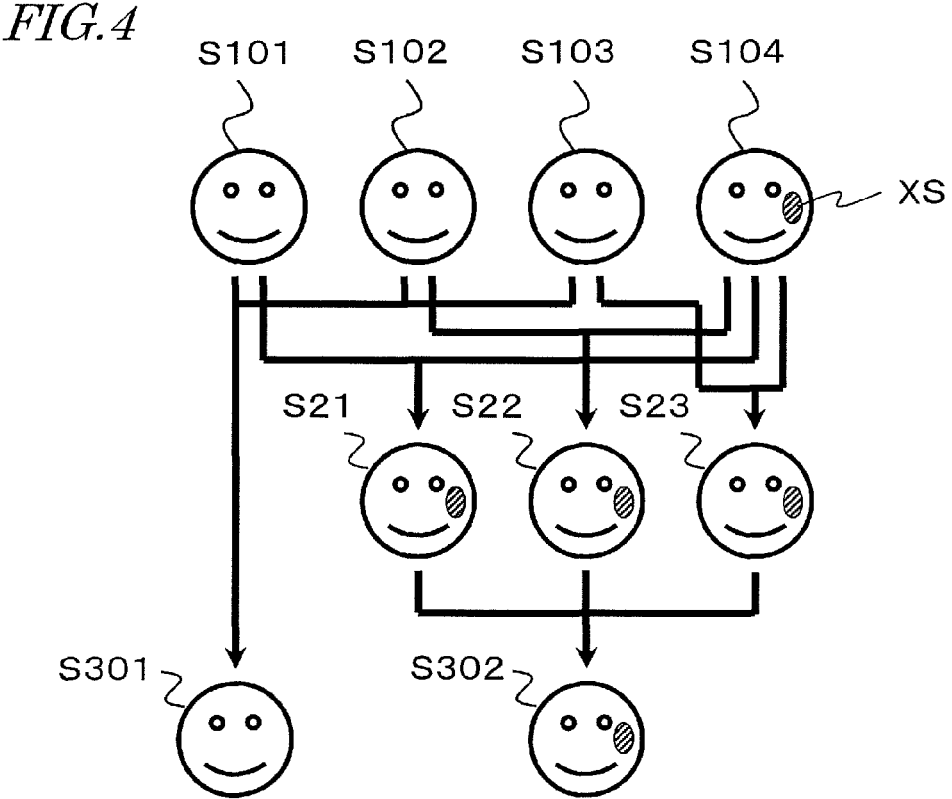
FIG. 4 is a schematic representation illustrating what image processing is carried out by the imaging device of the first embodiment.

This image processing may be schematically represented by the flow shown in FIG. 4. The first color image S301 is generated based on the first, second, and third pieces of image information S101, S102 and S103. This image processing may be carried out in the same way as generation of a color image based on R, G and B image information, for example by the first arithmetic processing section S201, just like color image processing by a general imaging device.

In this case, if there is a spot on the face skin of the object Ob, information about the spot XS captured will be included in the fourth piece of image information S104. By synthesizing each of the first, second, and third pieces of image information S101, S102 and S103 with the fourth piece of image information S104, pieces of image information S21, S22 and S23 are generated, respectively. This synthesis processing is suitably multiplication processing, for example. More specifically, the second arithmetic processing section S202 multiplies the grayscale values (representing luminance information) of pixels of each of the first, second, and third pieces of image information S101, S102 and S103 by the grayscale values of their associated pixels of the fourth piece of image information S104. Also, the second arithmetic processing section S202 performs the same processing as color image processing by a general imaging device on the pieces of image information S21, S22 and S23 thus obtained, thereby generating a second color image S302.

As shown in FIG. 4, information about the spot XS is included in the fourth piece of image information S104 yet to be synthesized. That is why if each of the first, second, and third pieces of image information S101, S102 and S103 is multiplied by the fourth piece of image information S104, information about the spot XS will be mirrored in each of these pieces of image information S21, S22 and S23. In addition, since the fourth piece of image information S104 is multiplied by each of the first, second, and third pieces of image information S101, S102 and S103, the second color image S302 can maintain its color ratio even after the synthesis. However, if only the multiplication processing is carried out, the entire image will get darker. For that reason, gamma correction may be performed after the multiplication. In addition, if gamma correction is carried out, then the saturation will decrease. That is why saturation enhancing processing may be carried out, too.

In addition, according to this embodiment, the first and second image capturing sections OS1 and OS2 are arranged so as to be spaced apart from each other, and therefore, parallax corresponding to an object distance will be produced between the images gotten by the first and second image sensors Na and Nb. If this parallax is a problem, the second arithmetic processing section may generate the pieces of image information S21, S22 and S23 after having generated parallax corrected image information for the fourth piece of image information S104. Specifically, the parallax to be produced between the third and fourth pieces of image information S103 and S104 obtained by the first and second image capturing sections OS1 and OS2 is extracted by performing pattern matching on each image on a micro-block basis, and then the image is shifted by the magnitude of the parallax that has been extracted on a micro-block basis. In this manner, the parallax corrected image information can be generated for the fourth piece of image information S104.

According to this embodiment, by adopting such a configuration for the imaging system and getting image processing done as described above, an ordinary color image and a color image, of which the spot portion is enhanced, can be obtained at the same time. That is why an ordinary image and a spot-enhanced color image can be gotten continuously and in parallel with each other, and a movie can be shot. As a result, this embodiment provides an imaging system which allows the viewer to observe a spot on the skin, for example, in real time.

In the embodiment described above, the fourth wavelength range is supposed to be the color violet wavelength range falling within the visible radiation range. However, the fourth wavelength range, as well as the third wavelength range, may also be the color blue wavelength range. That is to say, the center wavelength of the third and fourth wavelength ranges is shorter than that of the first and second wavelength ranges. Since the state of a spot can be checked even in the color blue range, a spot that can be seen to the naked eye can be captured in an even enhanced state.

Alternatively, the fourth wavelength range may also be a near-ultraviolet wavelength range. To capture an image falling within the near-ultraviolet wavelength range, a light source which can emit light that falls within the near-ultraviolet wavelength range is used as the polarized light source Qa. When the face skin is irradiated with a light beam falling within the near-ultraviolet wavelength range, the shooter suitably wears a pair of protective glasses to cut the ultraviolet ray. By using a light beam falling within the near-ultraviolet wavelength range, a hidden spot which is almost invisible to the naked eye can be shot.

Furthermore, if the imaging device of this embodiment is used under environmental light, the illuminating light emitted from the polarized light source Qa just needs to have components falling within the fourth wavelength range and oscillating in only the first direction.

In addition, the imaging system of this embodiment can obtain information about the cuticle region, and therefore, can be used effectively to observe not only the face skin but also the skin of various other parts of the given organism. Also, if the imaging system of this embodiment is applied to an endoscope, the state of a tissue which is located slightly inside the surface of the stomach or any other viscera can be observed. That is why the imaging system of this embodiment can also be used effectively in an endoscope.

Embodiment 2

Figure 5:
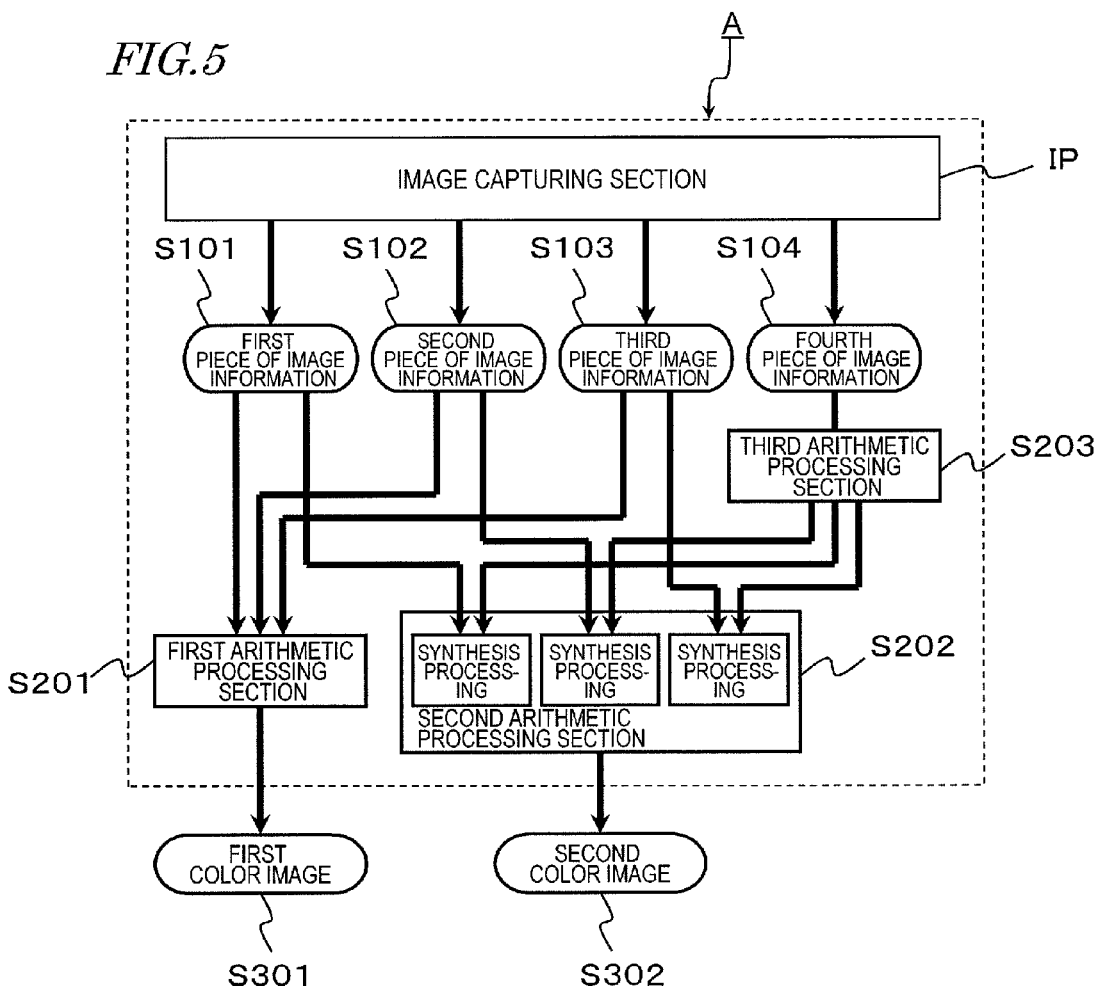
FIG. 5 is a block diagram illustrating an exemplary configuration for an imaging device for imaging systems according to second and third embodiments.

FIG. 5 is a block diagram illustrating an exemplary configuration for an imaging device for an imaging system according to this second embodiment. In the imaging system of this embodiment, the imaging device further includes a third arithmetic processing section, which is a major difference from the first embodiment. Thus, the following description of this second embodiment will be focused on that third arithmetic processing section.

In this embodiment, the third arithmetic processing section is configured to process the fourth piece of image information S104 so as to enhance the contrast of an image to be obtained based on the fourth piece of image information S104. After that, the fourth piece of image information S104 which has had its contrast enhanced will be synthesized with the first, second, and third pieces of image information S101, S102 and S103 by the second arithmetic processing section S202.

Figure 6:
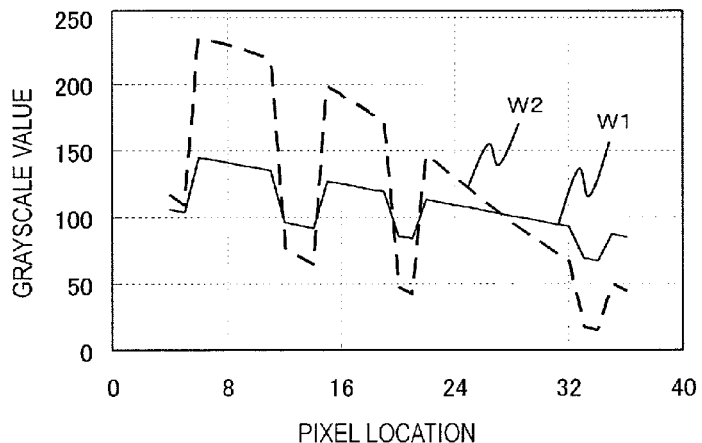
FIG. 6 is a graph showing how to enhance the contrast according to the second embodiment.

FIG. 6 is a graph showing how to enhance the contrast. Even though the image is actually a two-dimensional one, an image yet to have its contrast enhanced and a contrast-enhanced image will be described using one-dimensional grayscale values to make this description easily understandable. In the graph shown in FIG. 6, the abscissa represents a pixel location on the image sensor and the ordinate represents a grayscale value. The solid graph represents the grayscale value W1 of the face skin according to the fourth piece of image information S104 yet to be subjected to the contrast enhancing processing. At a grayscale value W1, a depressed portion of the curve indicates that there is a spot and the grayscale value decreases there. On the other hand, the dashed graph represents the grayscale value W2 according to the fourth piece of image information S104 that has been subjected to the contrast enhancing processing. By subjecting the fourth piece of image information S104 to contrast enhancing processing, the depressed portions of the grayscale value W2 get deeper and the difference in grayscale value between the spot portions and the other portions increases. As a result, a fourth piece of image information S104 in which the state of the spot has been further enhanced can be obtained. Consequently, by synthesizing each of the first, second, and third pieces of image information S101, S102 and S103 with the fourth piece of image information S104, a color image representing the spot in a more easily sensible state can be generated.

Embodiment 3

FIG. 5 is a block diagram illustrating an exemplary configuration for an imaging device for an imaging system according to this embodiment. In the imaging system of this embodiment, the third arithmetic processing section performs normalization processing before carrying out the contrast enhancing processing, which is a major difference from the second embodiment. Thus, the following description of this third embodiment will be focused on that normalization processing to be performed by the third arithmetic processing section.

In a situation where the grayscale value W1 has a gradient in the image represented by the fourth piece of image information S104 yet to be subjected to the contrast enhancing processing as indicated by the solid graph in FIG. 6, if the contrast enhancing processing was carried out as it is, the contrast would be enhanced everywhere, not just in the spot portion. As a result, in the resultant synthetic image, the shade of the image would get deeper in not only the spot portion but also everywhere else. That is why particularly when the object is irradiated unevenly with the illuminating light, the resultant synthetic image could look unnatural in some cases. Conversely, if the user tried to enhance the contrast to the point that the resultant image will not look unnatural, then the degree of contrast enhancement of the spot portion would be limited.

To get a natural image by avoiding enhancing the contrast in this manner, according to this embodiment, the third arithmetic processing section normalizes the grayscale value of the fourth piece of image information S104 before enhancing the contrast. Specifically, the third arithmetic processing section calculates the average of grayscale values with respect to each image block of a predetermined size by reference to the fourth piece of image information S104 and adjusts the gain of the grayscale value of each pixel in an image block based on the ratio of a predetermined normalized grayscale value to the average.

The normalization processing mentioned above will be described in further detail with reference to FIGS. 7(a) through 7(c). For example, the normalization processing may be carried out by calculating the average of grayscale values on an eight-pixel-block basis, the ratio of a predetermined normalized grayscale value to the block-by-block average (normalized grayscale value/block-by-block average) is regarded as the gain of the image block, and the gain is multiplied by the grayscale value of each pixel. As a result of this processing, the average grayscale value that has been calculated on an eight-pixel-block basis becomes a predetermined normalized grayscale value. As shown in FIG. 7(a), the grayscale value W1 which had a gradient before being subjected to the contrast enhancement has its gradient decreased as indicated by the normalized grayscale value W1'. Nevertheless, since the gain is determined on a block basis, grayscale level differences are created at the block boundaries indicated by the arrows. Thus, by linearly interpolating the gain between the eight-pixel blocks to avoid such a situation, the normalized grayscale value becomes as indicated by W1" in FIG. 7(b) and the level differences can be eliminated.

If the normalized grayscale value W1" is further subjected to the contrast enhancing processing, the contrast-enhanced grayscale value will be as indicated by W2" in FIG. 7(c). As a result, a fourth piece of image information S104, of which the grayscale value is enhanced only at a depressed portion representing a spot, can be obtained.

By carrying out the processing described above, even if the grayscale value had a gradient before being subjected to the contrast enhancement, the resultant synthetic image can be enhanced only in the spot portion. That is to say, the resultant synthetic color image will be an image, of which only the spot portion is enhanced just as intended.

Embodiment 4

FIG. 8 illustrates a configuration for an image capturing unit IP for an imaging system according to this fourth embodiment. The imaging system of this embodiment includes an image capturing unit IP which has a different structure from its counterpart of the first embodiment. That is why the following description of this fourth embodiment will be focused on that image capturing unit IP. The image capturing unit IP of the imaging device of this embodiment includes a lens optical system L, a half mirror which splits the optical path, a first image sensor Na, a band-pass filter F which transmits mostly a light beam falling within the fourth wavelength range, a second polarization filter PL2 which transmits mostly a light beam that oscillates parallel to the second polarization axis, and a second image sensor Nb.

In capturing an image of an object (not shown), the light beam that has come from the object passes through the lens optical system L and then reaches the half mirror HM, which has an optical path splitting structure and which splits the light beam into a light beam traveling toward the first image sensor Na and a light beam traveling toward the second image sensor Nb. The light beam that has traveled toward the first image sensor Na reaches the first image sensor Na as it is. On the other hand, the light beam that has traveled toward the second image sensor Nb reaches the second image sensor Nb after having been transmitted through the band-pass filter F which mainly transmits light falling within the fourth wavelength range and the second polarization filter PL2 which mainly transmits light oscillating in the second polarization axis direction in this order.

The first image sensor Na is a color image sensor as already described for the first embodiment, and obtains first, second, and third pieces of image information S101, S102 and S103 including pieces of information about light beams falling within the first, second, and third wavelength ranges. Meanwhile, the second image sensor Nb is a monochrome image sensor, and obtains image information S104 including a piece of information about a light beam falling within the fourth wavelength range and a piece of information about a light beam oscillating in the second polarization axis direction.

By using such a configuration, the first, second, third, and fourth pieces of image information S101, S102, S103 and S104 are obtained. The images may be synthesized together by performing the image processing that has already been described for any of the first, second, and third embodiments.

By adopting such a configuration, an imaging system that can get simultaneously an ordinary color image and a color image, of which the spot portion is enhanced, is realized as in the first embodiment described above.

In addition, since the optical path is split according to this embodiment by the half mirror, no parallax is produced between the images gotten by the first and second image sensors Na and Nb, unlike the first embodiment. According to this embodiment, there is no need to carry out image processing to correct the parallax and the circuit size of the second image processing section can be reduced.

Although a half mirror is supposed to be used according to this embodiment as an element of splitting the optical path, a dichroic mirror may be used instead of the half mirror. If a dichroic mirror is used, the imaging system may be designed so that the wavelength ranges of light beams to be transmitted are the first, second, and third wavelength ranges and that the wavelength range of a light beam to be reflected is the fourth wavelength range. If such a configuration is adopted, only a light beam falling mostly within the fourth wavelength range travels toward the second image sensor, and no band-pass filter F has to be used. As a result, a decrease in the quantity of light incident on the second image sensor Nb can be minimized and the shooting sensitivity can be increased.

Embodiment 5

FIG. 9 illustrates a configuration for an image capturing unit IP for an imaging system according to this fifth embodiment. The imaging system of this embodiment includes an image capturing unit IP which has a different structure from its counterpart of the first embodiment. Thus, the following description of this fifth embodiment will be focused on that image capturing unit IP. The image capturing unit IP of the imaging device of this embodiment includes a fly-eye lens LL, a band-pass filter F1 which transmits mostly a light beam falling within the first wavelength range, a band-pass filter F2 which transmits mostly a light beam falling within the second wavelength range, a band-pass filter F3 which transmits mostly a light beam falling within the third wavelength range, a band-pass filter F4 which transmits mostly a light beam falling within the fourth wavelength range, a polarization filter PL2 which transmits mostly a light beam oscillating in the second polarization axis direction, and an image sensor Nc.

In the fly-eye lens LL, four lens optical systems are arranged to form an array. Specifically, four lens optical systems La1, La2, La3 and La4 are arranged in two columns and two rows on the same plane. Meanwhile, on the image capturing plane Ni on the image sensor Nc, image capturing areas Ni1, Ni2, Ni3 and Ni4 have been defined so as to face one to one the lens optical systems La1, La2, La3 and La4, respectively.

The light that has been emitted from the polarized light source Qa is reflected from an object, and the reflected light is condensed by the lens optical systems La1, La2, La3 and La4, thereby producing object images in their associated image capturing areas Ni1, Ni2, Ni3 and Ni4 of the image sensor Nc. The band-pass filters F1, F2, F3 and F4 are arranged on the optical paths of the lens optical systems La1, La2, La3 and La4, respectively. As a result, an object image is produced in the image capturing area Ni1 via the lens optical system La1 and the band-pass filter F1 which transmits mostly a light beam falling within the first wavelength range. In the same way, another object image is produced in the image capturing area Ni2 via the lens optical system La2 and the band-pass filter F2 which transmits mostly a light beam falling within the second wavelength range. Still another object image is produced in the image capturing area Ni3 via the lens optical system La3 and the band-pass filter F3 which transmits mostly a light beam falling within the third wavelength range. And yet another object image is produced in the image capturing area Ni4 via the lens optical system La4 and the band-pass filter F4 which transmits mostly a light beam falling within the fourth wavelength range. In this manner, the image capturing unit IP shoots the object (not shown) through these four optical paths. By adopting such a configuration, first, second, and third pieces of image information S101, S102 and S103 including pieces of information about light beams falling within the first, second, and third wavelength ranges, respectively, and a fourth piece of image information S104 including a piece of information about a light beam falling within the fourth wavelength range and oscillating in the second polarization axis direction are obtained from the image capturing areas Ni1, Ni2, Ni3 and Ni4, respectively.

According to this embodiment, the lens optical systems La1, La2, La3 and La4 are arranged so as to be spaced apart from each other, and therefore, parallax corresponding to the object distance is produced between the images captured by the image capturing areas Ni1, Ni2, Ni3 and Ni4. If this parallax is a problem, the first and second arithmetic processing sections may each generate a color image after having corrected the parallax. Specifically, using the first piece of image information S101 as a reference image, parallax corrected images of second, third and fourth pieces of image information S102, S103 and S104 may be generated and then synthesized together. As already described for the first embodiment, an image portion may be extracted by performing pattern matching on each image on a micro-block basis, and then the image may be shifted by the magnitude of the parallax that has been extracted on a micro-block basis. In this manner, the parallax corrected image information can be generated.

By using such a configuration, first, second, third and fourth pieces of image information S101, S102, S103 and S104 can be obtained. The images may be synthesized together by performing the image processing that has already been described for any of the first, second, and third embodiments.

By adopting such a configuration, an imaging system that can get simultaneously an ordinary color image and a color image, of which the spot portion is enhanced, is realized as in the first embodiment described above. This fifth embodiment has a configuration in which the fly-eye lens LL is arranged on the single image sensor Nc. That is why compared to the configurations of the first and fourth embodiments, the image capturing unit IP can have a smaller volume and the imaging device can have a smaller overall size.

Embodiment 6

FIG. 10(a) illustrates a configuration for an image capturing unit IP for an imaging system according to this sixth embodiment. The imaging system of this embodiment includes an image capturing unit IP which has a different structure from its counterpart of the first embodiment. Thus, the following description of this sixth embodiment will be focused on that image capturing unit IP.

The image capturing unit IP of the imaging device of this embodiment includes a lens optical system L and an image sensor Nd. FIG. 10(b) illustrates an arrangement of pixels on the image sensor Nd. On the image capturing plane of the image sensor Nd, arranged as pixels are a number of photoelectric conversion sections to form a two-dimensional array. In FIG. 10(b), a band-pass filter which transmits mostly a light beam falling within the first wavelength range is provided for the pixel Pa1 of one photoelectric conversion section. In the same way, band-pass filters which transmit mostly a light beam falling within the second wavelength range and a light beam falling within the third wavelength range, respectively, are provided for the pixels Pa2 and Pa3. On the other hand, a band-pass filter which transmits mostly a light beam falling within the fourth wavelength range and a polarization filter which transmits mostly a light beam oscillating in the second polarization axis direction are provided for the pixel Pa4. The band-pass filters provided for those pixels are implemented as an absorptive filter or a filter of a dielectric multilayer film, and the polarization filter is implemented as a wire-grid polarizer.

In shooting an object (not shown), the light beam that has come from the subject passes through the lens optical system L and then reaches the image sensor Nd. Since a band-pass filter which transmits mostly a light beam falling within the first wavelength range is provided for the pixel Pa1, the first piece of image information S101 including a piece of information about the light beam falling within the first wavelength range can be generated by extracting only the pixel Pa1. In the same way, by extracting the pixels Pa2 and Pa3, the second and third pieces of image information S102 and S103 including pieces of information about light beams falling within the second and third wavelength ranges, respectively, can be generated. On the other hand, since a band-pass filter which transmits mostly a light beam falling within the fourth wavelength range and a polarization filter which transmits mostly a light beam oscillating in the second polarization axis direction are provided for the pixel Pa4, the fourth piece of image information S104 including a piece of information about the light beam oscillating parallel to the second polarization axis and falling within the fourth wavelength range can be generated by extracting only the pixel Pa4.

By using such a configuration, the first, second, third and fourth pieces of image information S101, S102, S103 and S104 can be obtained. The images may be synthesized together by performing the image processing that has already been described for any of the first, second, and third embodiments.

By adopting such a configuration, an imaging system that can get simultaneously an ordinary color image and a color image, of which the spot portion is enhanced, is realized as in the first embodiment described above. This sixth embodiment has a configuration in which the lens optical system L is arranged on the single image sensor N. That is why compared to the configurations of the first and fourth embodiments, the image capturing unit IP can have a smaller volume and the imaging device can have a smaller overall size.

Embodiment 7

In this seventh embodiment, the image capturing unit IP of the imaging device A has a different configuration from its counterpart of the first, fourth, fifth and sixth embodiments described above. Thus, a detailed description of the common features between this embodiment and the first, fourth, fifth and sixth embodiments will be omitted herein.

FIG. 11 illustrates a configuration for an image capturing unit IP for an imaging system according to this embodiment. The imaging system of this embodiment includes an image capturing unit IP which has a different structure from its counterpart of the first embodiment. Thus, the following description of this embodiment will be focused on that image capturing unit IP. The image capturing unit IP of this embodiment includes a lens optical system Lx, of which the optical axis is indicated by V, an array of optical elements K which is arranged in the vicinity of the focal point of the lens optical system Lx, and a monochrome image sensor Ne.

The lens optical system Lx includes a stop S on which the light that has come from the object (not shown) is incident, an optical element L1p on which the light that has passed through the stop S is incident, and a lens L2 that the light that has passed through the optical element L1p enters. The lens optical system Lx has first, second, third and fourth optical regions D1, D2, D3 and D4.

The lens L2 may be comprised of either a single lens or multiple lenses. In the latter case, those lenses may be arranged separately in front of, and behind, the stop S. n the example illustrated in FIG. 11, the lens L2 is illustrated as a single lens.

FIG. 12(a) is a front view of the optical element L1s as viewed from the object side. The optical element L1s is arranged to cover the optical regions D1, D2, D3 and D4, which are four regions that have been divided by two lines that pass through the intersection of the optical axis V with a plane perpendicular to the optical axis V and that intersect each other at right angles in the plane that intersects with the optical axis V at right angles. In the lens optical system Lx, the optical regions D1, D2, D3 and D4 run parallel to the optical axis V. Portions of the optical element L1s which are located in these optical regions D1, D2, D3 and D4 have mutually different spectral transmittance characteristics. The optical element L1s is arranged between the stop S and the optical element L1p. In these optical regions D1, D2, D3 and D4, the optical element L1s has spectral transmittance characteristics which transmit mainly light beams falling within the first, second, third and fourth wavelength ranges, respectively. For example, the optical element L1s includes filters which have spectral transmittance characteristics that transmit mostly light beams falling within the first, second, third and fourth wavelength ranges in the optical regions D1, D2, D3 and D4, respectively.

FIG. 12(b) is a front view of the optical element L1p as viewed from the object side. The optical element L1p has a polarization filter which transmits mostly a light beam oscillating parallel to the second polarization axis in only the optical region D1 and has a glass plate which transmits a light beam that oscillates in any direction.

As shown in FIGS. 11, 12(a) and 12(b), light beams B1, B2, B3 and B4, which form part of the light that has come from the object, are transmitted through the optical regions D1, D2, D3 and D4, respectively.

FIG. 13 is a perspective view illustrating an array of optical elements K. On the surface of the array of optical elements K, optical elements M are arranged in a grating pattern so as to face the image sensor Ne. Each of these optical elements M2 has a curved cross section both longitudinally and transversally, and projects toward the image sensor N. As can be seen, these optical elements M are micro lenses and are arranged two-dimensionally in the same two directions as the photoelectric conversion sections of the image sensor Ne to make this array of optical elements K a micro lens array. Each optical element M corresponds to four photoelectric conversion sections which are arranged in the row and column directions.

FIG. 14(a) illustrates the array of optical elements K and the image sensor Ne on a larger scale, and FIG. 14(b) shows the relative position of the array of optical elements K with respect to the photoelectric conversion sections (pixels) on the image sensor N. The array of optical elements K is arranged so that the optical elements M on its surface face the image capturing plane Ni. On the image capturing plane Ni, the image sensor Ne has a plurality of color pixels P, each of which is comprised of four photoelectric conversion sections and which area arranged in the row and column directions. Specifically, each pixel P includes first, second, third and fourth photoelectric conversion sections which are arranged in the row and column directions, which sense the incident light and convert it into electrical signals independently of each other, and which form pixels Pb1, Pb2, Pb3 and Pb4.

The array of optical elements K is arranged in the vicinity of the focal point of the lens optical system Lx and at a predetermined distance from the image capturing plane Ni. As shown in FIG. 14(b), the center Mc of each of the optical elements M that form the array of optical elements K and the center Pc of its associated pixel P comprised of four photoelectric conversion sections are located on the same line that is parallel to the optical axis V. That is why each optical element M is arranged to face to its associated four photoelectric conversion sections.

On the image capturing plane Ni, micro lenses Ms are arranged so that each of those micro lenses Ms covers the surface of its associated first, second, third and fourth photoelectric conversion sections (i.e., pixels Pb1, Pb2, Pb3 and Pb4). Color filters with mutually different spectral transmittance characteristics or any other kind of elements are not arranged over those first, second, third and fourth photoelectric conversion sections (pixels Pb1, Pb2, Pb3 and Pb4).

The array of optical elements K is designed so that most of the light beams B1, B2, B3 and B4 which have passed through the optical regions D1, D2, D3 and D4 of the optical elements L1s and L1p reach the pixels P1, P2, P3 and P4 on the image capturing plane Ni. Specifically, by appropriately setting the refractive index of the array of optical elements K, the distance from the image capturing plane Ni, the radius of curvature of the surface of the optical elements M and other parameters, such a configuration is realized.

That is why mostly a light beam falling within the first wavelength range is incident on the pixel Pb1 and a first piece of image information S101 consisting essentially of only information about the light beam falling within the first wavelength range can be generated by extracting only the pixel Pb1. In the same way, second and third pieces of image information S102 and S103 consisting essentially of only information about the light beams falling within the second and third wavelength ranges, respectively, can be generated by extracting only the pixels Pb2 and Pb3, respectively. Meanwhile, mostly a light beam falling within the fourth wavelength range and oscillating parallel to the second polarization axis is incident on the pixel Pb4 and a fourth piece of image information S104 consisting essentially of only information about the light beam oscillating in the second polarization axis direction and falling within the fourth wavelength range can be generated by extracting only the pixel Pb4.

By using such a configuration, the first, second, third and fourth pieces of image information S101, S102, S103 and S104 can be obtained. The images may be synthesized together by performing the image processing that has already been described for any of the first, second, and third embodiments.

By adopting such a configuration, an imaging system that can get simultaneously an ordinary color image and a color image, of which the spot portion is enhanced, is realized as in the first embodiment described above.

According to this seventh embodiment, the configurations of the optical elements L1s and L1p can be changed according to the intended application. Among other things, the optical element L1s contributes to designing an intended spectral characteristic by using a dielectric multilayer film, and therefore, the spectral characteristic can be customized more easily.

Embodiment 8

FIG. 15 is a block diagram illustrating an exemplary configuration for an imaging device for an imaging system according to this eighth embodiment. The imaging system of this embodiment includes an image capturing section IP and an imaging device A which have different configurations from their counterparts of the first embodiment. That is why the following description will be focused on the image capturing section IP and the flow of image processing.

FIG. 15 is a block diagram illustrating an exemplary configuration for the imaging device A of this embodiment, which includes the image capturing section IP and fourth, fifth, sixth and seventh arithmetic processing sections S204, S205, S206 and S207.

FIG. 16 is a schematic representation illustrating an exemplary configuration for the image capturing section IP shown in FIG. 2. The image capturing section IP of this embodiment includes an additional polarization filter PL3 and makes each of the band-pass filters F3 and F4 transmit a light beam falling within the third wavelength range, which is a major difference from the fifth embodiment described above. The polarization filter PL3 transmits mostly a light beam oscillating in the first polarization axis direction, i.e., perpendicularly to the polarization filter PL2.

By adopting such a configuration, first and second pieces of image information S101 and S102 including pieces of information about light beams falling within the first and second wavelength ranges, respectively, a fifth piece of image information S105 including a piece of information about a light beam falling within the third wavelength range and oscillating in the first polarization axis direction, and a sixth piece of image information S106 including a piece of information about a light beam falling within the third wavelength range and oscillating in the second polarization axis direction that intersects at right angles with the first polarization axis are obtained from the image capturing areas Ni1, Ni2, Ni3 and Ni4, respectively.

Next, the image processing flow will be described. As shown in FIG. 15, the fourth arithmetic processing section S204 is configured to generate a seventh piece of image information including a piece of information about the third wavelength range by adding together the fifth and sixth pieces of image information S105 and S106 including pieces of information about light beams falling within the third wavelength range and oscillating in the first and second polarization axis directions, respectively. In this case, since the second polarization axis intersects at right angles with the first polarization axis, the seventh piece of image information turns into image information including a piece of information about non-polarized light falling within the third wavelength range as a result of the addition processing.

The fifth arithmetic processing section S205 is configured to generate a first piece of color information S301 based on the first, second and seventh pieces of image information S101, S102 and S107. In this image processing, a color image is generated based on R, G and B image information, for example.

The sixth arithmetic processing section S206 is configured to generate a third color image S303 by synthesizing (e.g., multiplying) together the first color image S301 and the fifth piece of image information S105. The fifth piece of image information S105 includes a piece of information about a light beam oscillating in the first polarization axis direction. Since the first polarization axis direction is the same as the polarization axis direction of the illuminating light, the fifth piece of image information S105 includes a lot of components of the light that has been specular reflected from the face skin. According to such image information including those components of the light that has been specular reflected from the surface of the face skin, the shadows representing the micro-geometry of the face skin are displayed more definitely, thus providing the viewer with an image which allows him or her to sense small wrinkles on the skin and so on more easily. That is why by performing such synthesis processing, a third color image S303 can be generated with those portions with the small wrinkles enhanced.

The seventh arithmetic processing section S207 is configured to generate a fourth color image S304 by synthesizing (e.g., multiplying) together the first color image S301 and the sixth piece of image information S106.

As already described for the first embodiment, the polarization filter PL2 cuts most of the components of the light that has been specular-reflected from the face skin (i.e., components representing unwanted shine of the face skin), and therefore, the spots on the face skin can be sensed more easily by reference to the sixth piece of image information S106. That is why by performing such synthesis processing, a fourth color image S304 can be generated with the spot portions enhanced as in the first embodiment described above.

As can be seen, according to this embodiment, by adopting such a configuration for the imaging system and performing such image processing, an ordinary color image, a color image in which spot portions are enhanced, and a color image in which portions with small wrinkles are enhanced can be gotten simultaneously. Consequently, an ordinary color image, a color image in which spot portions are enhanced, and a color image in which portions with small wrinkles are enhanced can be gotten continuously and in parallel with each other, and a movie can be shot. Consequently, an imaging system which allows the viewer to observe an image in which skin spots or wrinkles are enhanced in real time is realized.

It should be noted that the image capturing section of this eighth embodiment does not have to have the optical system shown in FIG. 16. Alternatively, the image capturing section may also be formed by arranging a polarization filter appropriately for the optical system of the sixth embodiment shown in FIG. 10 or the optical system of the seventh embodiment shown in FIG. 11.

INDUSTRIAL APPLICABILITY

The imaging system of the present invention can be used effectively as an imaging device such as a skin checkup camera or an endoscope camera, and is also applicable to an imaging system for a microscope or an electronic mirror.

REFERENCE SIGNS LIST

IP image capturing unit
A imaging device
AP imaging system
S101 to S104 image information
S201 to S203 arithmetic processing section
S301, S302 color image information
W1, W2 grayscale value
PL1, PL2 polarization filter
La, Lb, L lens
Na, Nb, Nc, Nd, Ne image sensor
LL fly-eye lens
La1 to La4 fly-eye lens' optical elements
F1 to F4 band-pass filter
Ni image capturing plane
Ni1 to Ni4 image capturing areas on image capturing plane
OS1, OS2 image capturing section
Pa1 to Pa4 pixels on image sensor
Lx lens optical system
L1$s$, L1$p$ optical element
L2 lens
D1 to D4 optical region
S stop
K array of optical elements
M optical element in array of optical elements
Ms micro lens on image sensor
Pb1 to Pb4 pixels on image sensor
Qa polarized light source

The invention claimed is:

1. An imaging system comprising:
    a polarized light source which emits illuminating light including a component of light that oscillates parallel to a first polarization axis;
    an image capturing unit which is configured to get, based on light beams that have returned at the same point in time from an object that is irradiated with the illuminating light, a first piece of image information including information about light beam that fall within a first wavelength range, a second piece of image information including information about light beam that fall within a second wavelength range, a third piece of image information including information about light beam that fall within a third wavelength range and a fourth piece of image information including information about light beam that fall within a fourth wavelength range, the light beam falling within the fourth wavelength range having been emitted from the polarized light source and reflected from the object, oscillating parallel to a second polarization axis that is different from the first polarization axis, and belonging to the same wavelength range as the component of the illuminating light;
    a first arithmetic processing section which is configured to generate a first piece of color image information based on the first, second and third pieces of image information; and
    a second arithmetic processing section which is configured to generate a second piece of color image information by synthesizing each of the first, second and third pieces of image information with the fourth piece of image information.

2. The imaging system of claim 1, wherein the center wavelength of the fourth wavelength range is shorter than the center wavelength of any of the first, second and third wavelength ranges.

3. The imaging system of claim 1, wherein the fourth wavelength range is the same as the third wavelength range and the center wavelength of the third and fourth wavelength ranges is shorter than the center wavelength of any of the first and second wavelength ranges.

4. The imaging system of claim 1, wherein each of the first, second, third and fourth wavelength ranges is a visible radiation wavelength range.

5. The imaging system of claim 1, wherein each of the first, second, and third wavelength ranges is a visible radiation wavelength range and the fourth wavelength range is a near-ultraviolet wavelength range.

6. The imaging system of claim 1, further comprising a third arithmetic processing section which is configured to perform the processing of enhancing the contrast of the fourth piece of image information before the second arithmetic processing section performs the synthesis processing.

7. The imaging system of claim 6, wherein before enhancing the contrast, the third arithmetic processing section calculates the average of grayscale values for each image block with a predetermined size with respect to the fourth piece of image information, and adjusts the gain of the grayscale value of each pixel in the image block based on the ratio of a predetermined normalized grayscale value to the average.

8. The imaging system of claim 1, wherein the synthesis processing includes multiplication processing.

9. The imaging system of claim 1, wherein the image capturing unit includes first and second image sensors,
the first, second and third pieces of image information are obtained by the first image sensor, and
the fourth piece of image information is obtained by the second image sensor.

10. The imaging system of claim 9, wherein the image capturing unit further includes an optical path splitting structure which splits a light beam that has come from the object into an optical path leading to the first image sensor and another optical path leading to the second image sensor.

11. The imaging system of claim 1, wherein the image capturing unit includes an image sensor, and
the image sensor gets the first, second, third and fourth pieces of image information.

12. The imaging system of claim 11, wherein the image capturing unit further includes:
a lens array in which four lenses are arranged to form an array; and
a spectral filter which transmits information about light beams falling within the first through fourth wavelength ranges and which is arranged so that those four light beams are associated one to one with respective optical paths of the four lenses, and
the image sensor has four image capturing areas which are associated one to one with the four lenses.

13. The imaging system of claim 11, wherein the image sensor includes:
a plurality of photoelectric conversion sections which are arranged in a planar pattern;
first to fourth spectral filters which are arranged on the plurality of photoelectric conversion sections to transmit the light beams falling within the first to fourth wavelength ranges, respectively; and
a polarization filter which is arranged on a photoelectric conversion section where the fourth spectral filter is arranged and which have the second polarization axis.

14. The imaging system of claim 11, wherein the image capturing unit includes:
a lens optical system; and
an array of optical elements which is arranged between the lens optical system and the image sensor,
the image sensor includes first, second, third and fourth sets of photoelectric conversion sections on which light that has passed through the lens optical system is incident,
the lens optical system has four optical regions which include first, second, third and fourth optical regions that transmit light beams falling within the first, second, third and fourth wavelength ranges, respectively, the fourth optical region transmitting mostly a light beam oscillating parallel to the second polarization axis, and
the array of optical elements makes the light beams that have passed through the first, second, third and fourth optical regions incident onto the first, second, third and fourth sets of photoelectric conversion sections, respectively.

15. The imaging system of claim 1, further comprising a display device which displays the image that has been gotten by the image capturing section.

16. The imaging system of claim 1, wherein the polarized light source includes a light source which emits light falling within the visible radiation wavelength range and a polarization filter which is arranged to transmit the light that has been emitted from the light source and which has a first polarization axis.

17. The imaging system of claim 1, wherein the polarized light source includes four light sources which emit light beams falling within the first, second, third and fourth wavelength ranges, respectively, and a polarization filter which has a first polarization axis, and
the polarization filter is arranged so that only the light beam that has come from the light source that emits the light beam falling within the fourth wavelength range is transmitted through the polarization filter.

18. An imaging system comprising:
a polarized light source which emits illuminating light including a component of light that oscillates parallel to a first polarization axis;
an image capturing unit which is configured to get, based on light beams that have returned at the same point in time from an object that is irradiated with the illuminating light, a first piece of image information including information about light beam that fall within a first wavelength range, a second piece of image information including information about light beam that fall within a second wavelength range, a fifth piece of image information including information about light beam that fall within a third wavelength range, the light beam having been emitted from the polarized light source and reflected from the object and oscillating parallel to the first polarization axis, and a sixth piece of image information including information about light beam that fall within third wavelength range, the light beam having been emitted from the polarized light source and reflected from the object and oscillating parallel to a second polarization axis that is different from the first polarization axis;
a fourth arithmetic processing section which is configured to generate a seventh piece of image information, including a piece of information about the light beam falling within the third wavelength range, based on the fifth and sixth pieces of image information;

a fifth arithmetic processing section which is configured to generate a first piece of color image information based on the first, second and seventh pieces of image information;

a sixth arithmetic processing section which is configured to generate a third piece of color image information by synthesizing the first piece of color image information and the fifth piece of image information together; and a seventh arithmetic processing section which is configured to generate a fourth piece of color image information by synthesizing the first piece of color image information and the sixth piece of image information together.

* * * * *